US 9,945,917 B2

(12) United States Patent
Drake et al.

(10) Patent No.: US 9,945,917 B2
(45) Date of Patent: Apr. 17, 2018

(54) ENHANCED NUCLEAR QUADRUPOLE RESONANCE AND GROUND PENETRATING RADAR USING METAMATERIAL ANTENNA

(71) Applicant: LOCKHEED MARTIN CORPORATION, Bethesda, MD (US)

(72) Inventors: Christina Hartsell Drake, Orlando, FL (US); Clara Rivero Baleine, Orlando, FL (US); Nelson Ch Poon, Palmdale, CA (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 897 days.

(21) Appl. No.: 14/150,704

(22) Filed: Jan. 8, 2014

(65) Prior Publication Data

US 2015/0260812 A1    Sep. 17, 2015

Related U.S. Application Data

(60) Provisional application No. 61/750,268, filed on Jan. 8, 2013.

(51) Int. Cl.
| | |
|---|---|
| *G01R 33/34* | (2006.01) |
| *G01R 33/44* | (2006.01) |
| *G01N 24/08* | (2006.01) |
| *G01R 33/36* | (2006.01) |

(52) U.S. Cl.
CPC ..... *G01R 33/441* (2013.01); *G01R 33/34092* (2013.01); *G01N 24/084* (2013.01); *G01R 33/3635* (2013.01)

(58) Field of Classification Search
CPC ............ G01R 33/441; G01R 33/34092; G01R 33/3635; G01N 24/084
See application file for complete search history.

(56) References Cited

U.S. PATENT DOCUMENTS

| 5,826,178 A | 10/1998 | Owen |
|---|---|---|
| 6,326,783 B1 | 12/2001 | Tanaka |
| 6,493,551 B1 | 12/2002 | Wang et al. |
| 6,795,037 B2 | 9/2004 | Greim |
| 6,806,710 B1 | 10/2004 | Renz et al. |

(Continued)

FOREIGN PATENT DOCUMENTS

| EP | 2458396 | 5/2012 |
|---|---|---|
| ES | 2344391 | 8/2010 |

(Continued)

OTHER PUBLICATIONS

McDermott et al., "Microtesla MRI with a Superconducting Quantum Interference Device" PNAS May 25, 2004, vol. 101 No. 21 7857-7861.

(Continued)

*Primary Examiner* — Clayton E Laballe
*Assistant Examiner* — Ruifeng Pu
(74) *Attorney, Agent, or Firm* — Terry M. Sanks, Esq.; Beusse Wolter Sanks & Maire, PLLC

(57) ABSTRACT

A method and system for enhanced NQR or GPR include a metamaterial antenna configured to both transmit and receive a magnetic field focused at a near-field distance separated from the antenna at a corresponding antenna frequency corresponding to a nuclear quadrupole resonance frequency of an atom in a target material.

16 Claims, 19 Drawing Sheets

(56) References Cited

U.S. PATENT DOCUMENTS

| | | | |
|---|---|---|---|
| 6,985,118 | B2 | 1/2006 | Zarro et al. |
| 7,242,364 | B2 | 7/2007 | Ranta |
| 7,345,475 | B2 | 3/2008 | Takeuchi et al. |
| 7,366,701 | B2 | 4/2008 | Werner et al. |
| 7,501,823 | B2 | 3/2009 | Nistler et al. |
| 7,532,008 | B2 | 5/2009 | Pendry et al. |
| 7,623,745 | B2 | 11/2009 | Podolskiy et al. |
| 7,626,392 | B2 | 12/2009 | Nistler et al. |
| 7,688,070 | B2 | 3/2010 | Weyers et al. |
| 7,710,336 | B2 | 5/2010 | Schweizer et al. |
| 7,808,722 | B2 | 10/2010 | Tonucci |
| 7,864,394 | B1 | 1/2011 | Rule et al. |
| 8,212,880 | B2 | 7/2012 | Anderson et al. |
| 9,194,750 | B2 | 11/2015 | Oster et al. |
| 2004/0244625 | A1 | 12/2004 | Tiernan et al. |
| 2006/0255275 | A1 | 11/2006 | Garman et al. |
| 2007/0200566 | A1* | 8/2007 | Clark ............... G01V 5/0008 324/318 |
| 2008/0165079 | A1* | 7/2008 | Smith ............... B82Y 20/00 343/911 R |
| 2009/0040131 | A1 | 2/2009 | Mosallaei |
| 2009/0096545 | A1 | 4/2009 | O'Hara et al. |
| 2009/0099623 | A1 | 4/2009 | Bentwich |
| 2009/0140946 | A1 | 6/2009 | Ziolkowski et al. |
| 2009/0156976 | A1 | 6/2009 | Korbling et al. |
| 2009/0201221 | A1 | 8/2009 | Werner et al. |
| 2009/0224862 | A1 | 9/2009 | Pao et al. |
| 2009/0284644 | A1 | 11/2009 | McKaughan et al. |
| 2010/0003197 | A1 | 1/2010 | Bikram |
| 2010/0009704 | A1 | 1/2010 | Fan et al. |
| 2010/0133488 | A1 | 6/2010 | Giakos |
| 2010/0239504 | A1 | 9/2010 | Liu et al. |
| 2010/0259345 | A1 | 10/2010 | Kim et al. |
| 2011/0074425 | A1 | 3/2011 | Chu et al. |
| 2011/0077506 | A1 | 3/2011 | Driehuys et al. |
| 2011/0204891 | A1 | 8/2011 | Drake et al. |
| 2011/0209110 | A1 | 8/2011 | Grbic et al. |
| 2011/0267244 | A1* | 11/2011 | Rajgopal ............... H01Q 1/38 343/720 |
| 2011/0279681 | A1 | 11/2011 | Cabib et al. |
| 2011/0287218 | A1* | 11/2011 | Narimanov ............ G02B 1/002 428/141 |
| 2012/0082441 | A1 | 4/2012 | Krueger |
| 2012/0105061 | A1* | 5/2012 | Drake ............... G01R 33/10 324/318 |
| 2012/0105267 | A1* | 5/2012 | DeLia ............... G01S 13/86 342/22 |
| 2012/0211665 | A1 | 8/2012 | Cloud et al. |
| 2012/0228563 | A1* | 9/2012 | Fuller ............... F41H 13/0043 252/582 |
| 2013/0002253 | A1* | 1/2013 | Werner ............... G01R 33/36 324/322 |
| 2013/0127463 | A1 | 5/2013 | Matschl et al. |
| 2013/0187647 | A1* | 7/2013 | Walsh ............... G01N 24/081 324/303 |
| 2014/0152486 | A1* | 6/2014 | Apostolos ............ G01S 13/885 342/22 |

FOREIGN PATENT DOCUMENTS

| | | |
|---|---|---|
| GB | 2363645 | 1/2002 |
| KR | 10-2008-0004706 | 1/2008 |

OTHER PUBLICATIONS

Freire et al., "On the Application of μr=−1 Metamaterial Lenses for Magnetic Resonance Imaging" Journal of Magnetic Resonance, vol. 203, No. 1, Mar. 1, 2010, pp. 81-90.

Iyer et al., "A Three Dimensional Isotropic Transmission Line Metamaterial Topology for Free-Space Excitation" Applied Physics Letters, AIP, American Institute of Physics Melville, NY vol. 92, No. 26, Jul. 1, 2008 pp. 1-3.

Jiang et al., "An Isotropic 8.5 MHz Magnetic Meta-Lens" Antennas and Propagation (Apsursi), 2011 IEEE International Symposium on, IEEE, Jul. 3, 2011, pp. 1151-1154.

Pendry et al., "Magnetism From Conductors and Enhanced Non-linear Phenomena" IEEE Transactions on Microwave Theory and Techniques, IEEE Service Center, Piscataway, NJ, vol. 47, No. 11 Nov. 11, 1999.

Babu et al., :Electron Paramagnetic Study on Radical Scavenging Properties of Ceria Nancparticles Chemical Physics Letters, 442, pp. 405-408 (2007).

Freire et al., Experimental Demonstration of a μ=−1 Metamaterial Lens for Magnetic Resonance Imaging: Applied Physics Letters, vol. 93 pp. 1-3 (2008).

Patil et al., "Protein Adsorption and Cellular Uptake of Cerium Oxide Nanoparticles as a Function of Zeta Potential" Biomaterials 28, pp. 4600-4607 (2007).

J.B. Pendry, "Negative Refraction Makes a Perfect Lens" Physical Review Letters vol. 85, No. 18, Oct. 30, 2000, pp. 3966-3969.

Tarnuzzer et al., "Vacancy Engineered Ceria Nanostructures for Protection from Radiation-Induces Cellular Damage" Nano Letters, vol. 5, No. 12, pp. 2573-2577 (2005).

Zotev et al., "Microtesla MRI of the Human Brain Combined with MEG", Los Alamos National Laboratory, Applied Modern Physics Group, MS D454, pp. 1-8.

Volakis et al., "Small Wideband and Conformal Metamaterial Antennas and Arrays" Dec. 8, 2010 pp. 1-48.

Erentaok et al., Lumped Element Capacitor Based Two-Demensional Efficient Metamaterial-Inspired Electrically-Small Antenna, 2007, pp. 19-22.

Wiltshire et al., "Microstructured Magnetic Materials for RF Flux Guides in Magnetic Resonance Imaging" Science, 291, 849 (2001).

Freire et al., "Planar Magnetoinductive Lens for Three-Dimensional Subwavelength Imaging" Appl. Phys. Lett., 86, 182505 (2005).

Lapine et al., "Realistic Metamaterial Lenses: Limitations Imposed by Discrete Structure" Physical Review B, 82 165124 (2010).

C.P. Scarborough, "Experimental Demonstrations of an Isotropic Metamaterial Super Lens with Negative Unity Permeability at 8.5 MHz" Applied Physics Letters, 10191), 2, (2012).

Goussetis et al., Periodcially Loaded Dipole Array Supporting left-Handed Propagation: IEE Proc.-Microw Antennas Propag., vol. 152, No. 4, Aug. 2005.

Guven et al., Near Field Imaging in Microwave Regime Using Double Layer Split-Ring Resonator Based metamaterials, Optoelectronics Review 14:3, pp. 213-216.

Jelinek et al., "A Magnetic Metamaterial Composed of Randomly Oriented SRRs" Piers Online, vol. 2, No. 6, 2006, pp. 624-627.

Penciu et al., "Multi-Gap Individual and Coupled Split-Ring Resonator Structures" Optics Express, vol. 16, No. 22, Oct. 27, 2008, pp. 18131-18144.

* cited by examiner

ARTIFICIAL TRANSMISSION LINE (ATL)

SLOW DOWN CURRENTS FLOWING ON ANTENNA, USING INDUCTIVE AND CAPACITIVE LOADING $$v_g = \frac{1}{\sqrt{L_{eff} C_{eff}}} \quad , \quad Z = \sqrt{\frac{L_{eff}}{C_{eff}}}$$

LOAD ANTENNA NEAR FIELDS WITH MATERIAL $\varepsilon_r, \mu_r$ $$\nabla^2 E + \omega^2 \mu_{eff} \varepsilon_{eff} = 0 \quad , \quad Z_w = \sqrt{\frac{\mu_{eff}}{\varepsilon_{eff}}}$$

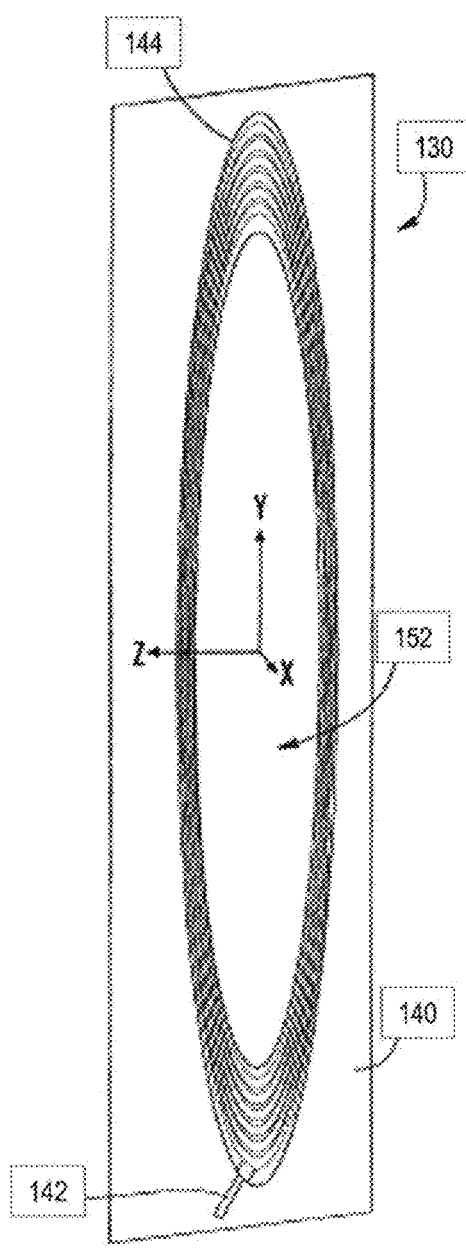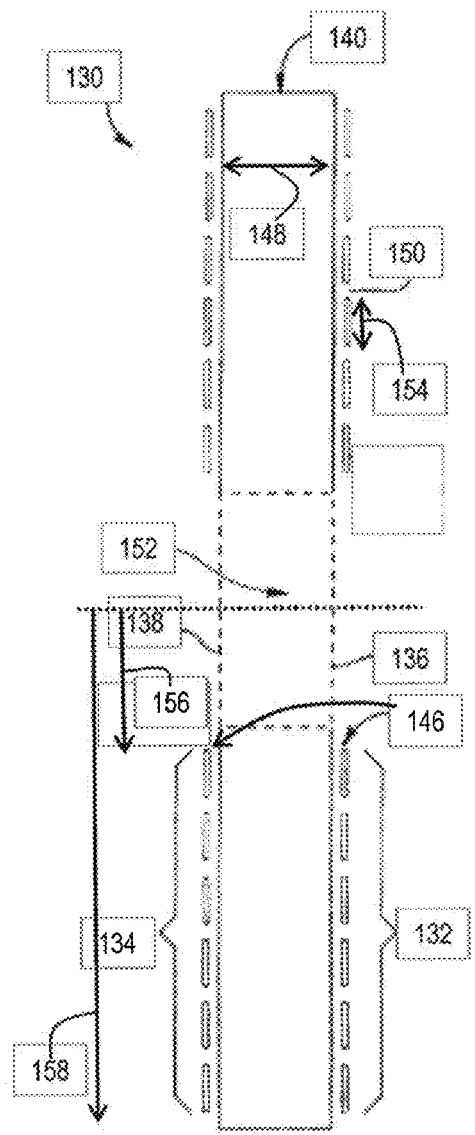
FIG. 1D
FIG. 1E

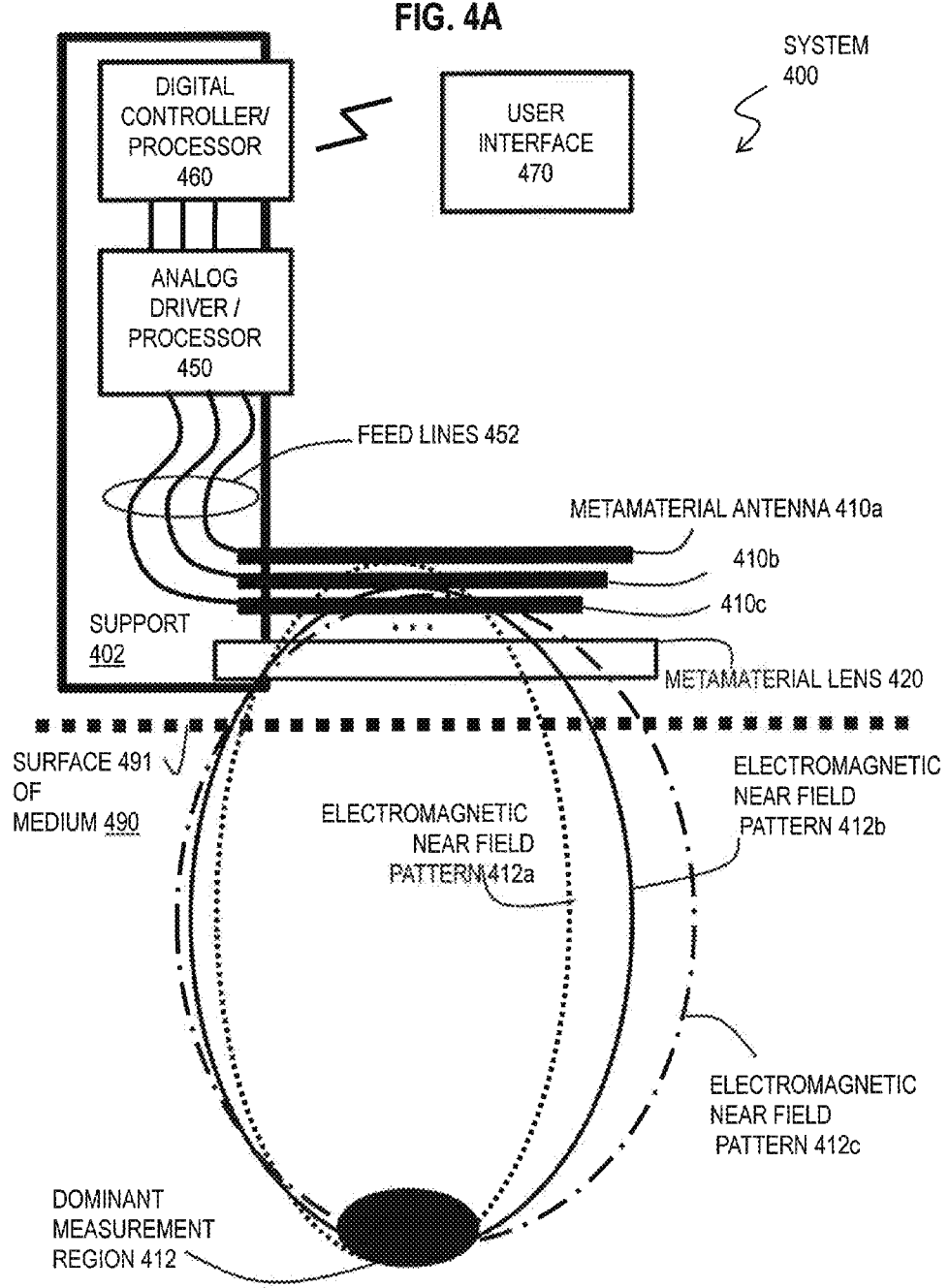

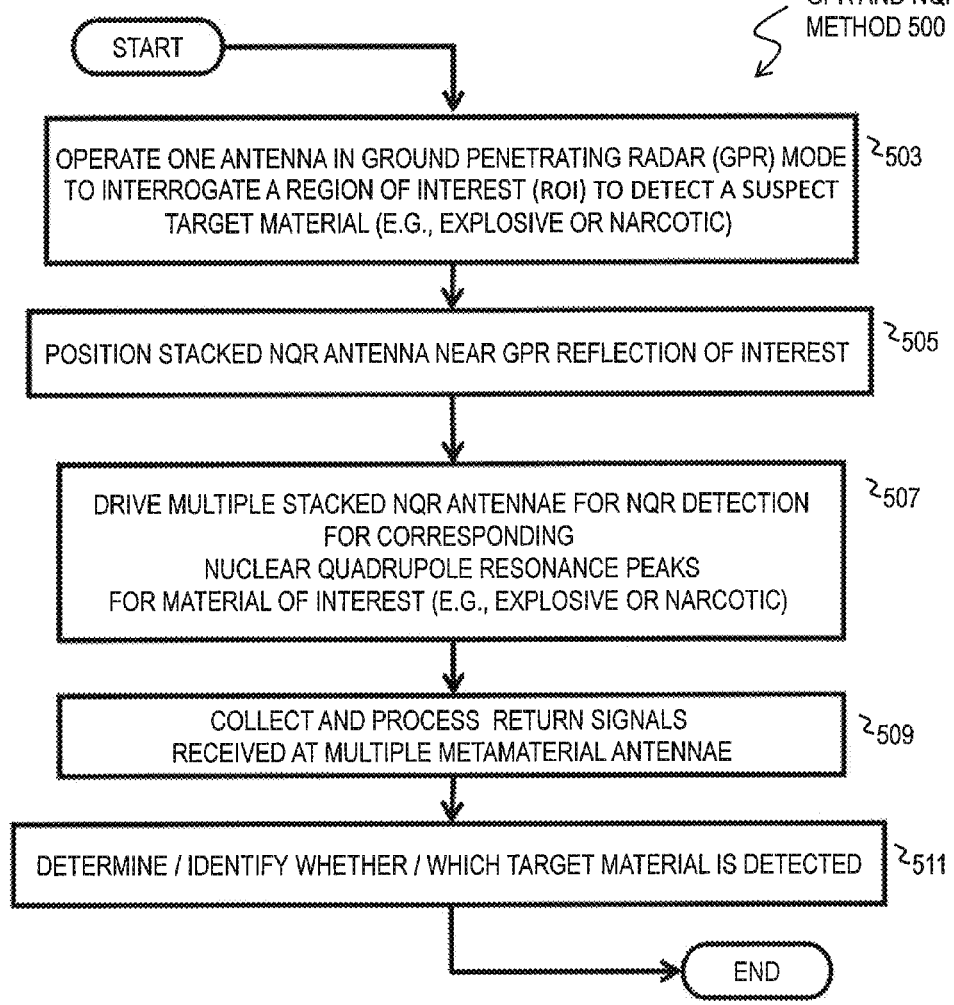

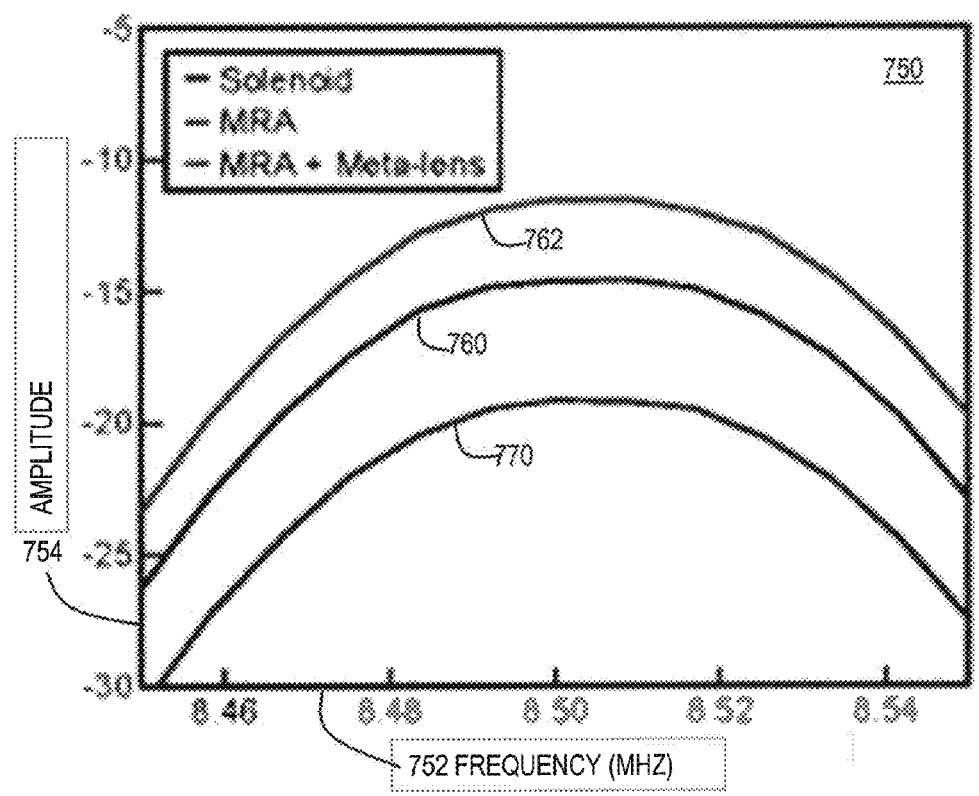

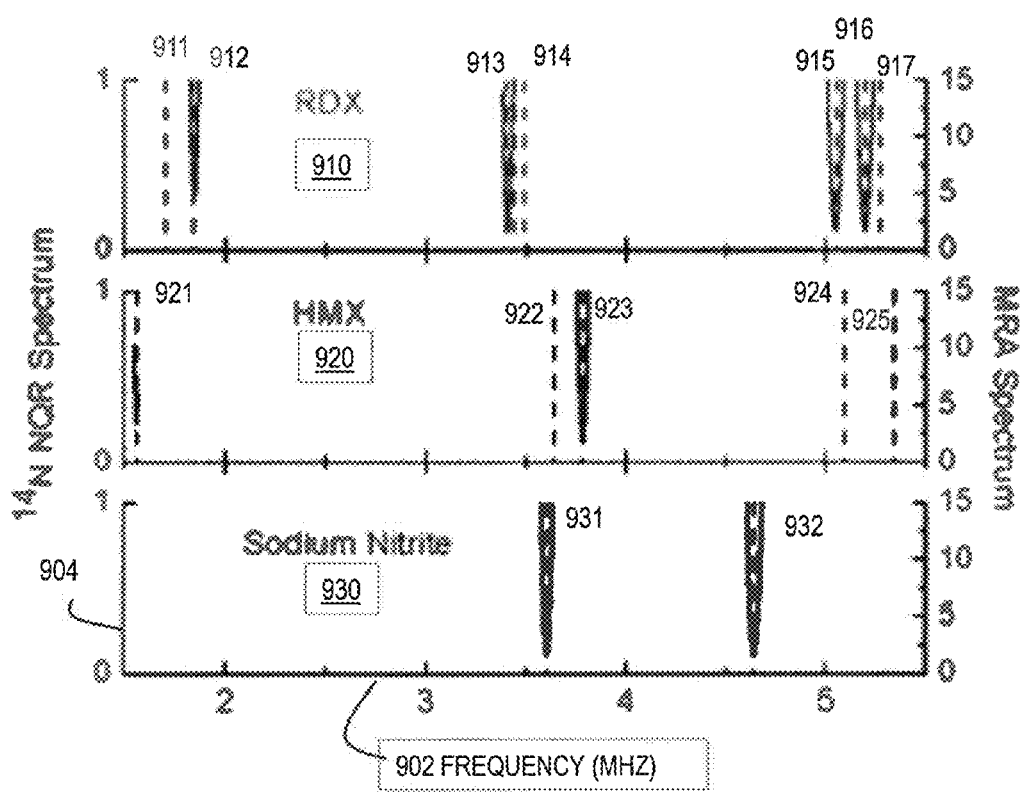

ENHANCED NUCLEAR QUADRUPOLE RESONANCE AND GROUND PENETRATING RADAR USING METAMATERIAL ANTENNA

CROSS-REFERENCE TO RELATED APPLICATIONS

This application claims the benefit of U.S. Provisional Application No. 61/750,268 filed Jan. 8, 2013, the entire contents of which are hereby incorporated by reference as if fully set forth herein, under 35 U.S.C. § 119(e).

BACKGROUND

Nuclear magnetic resonance (NMR) studies certain nuclei by aligning them with an applied constant magnetic field ($B_0$) and perturbing this alignment using an alternating magnetic field ($B_1$), orthogonal to the constant magnetic field. The resulting response to the perturbing magnetic field is the phenomenon that is exploited in magnetic resonance spectroscopy (MRS) and magnetic resonance imaging (MRI).

In contrast to NMR, nuclear quadrupole resonance (NQR) transitions of nuclei can be detected in the absence of a magnetic field, and for this reason NQR spectroscopy is referred to as "zero Field NMR." The NQR resonance is related to the interaction of an electric field gradient (EFG) with the quadrupole moment of the nuclear charge distribution. Because the EFG at the location of a nucleus in a given substance is determined primarily by the valence electrons involved in the particular bond with other nearby nuclei, the NQR frequency at which transitions occur is unique for a given substance. A particular NQR frequency in a compound or crystal is proportional to the product of the nuclear quadrupole moment, a property of the nucleus, and the EFG in the neighborhood of the nucleus. It is this product which is termed the nuclear quadrupole coupling constant for a given isotope in a material and can be found in tables of known NQR transitions.

One application of NQR is for the detection of non-metallic chemical compounds hidden in an opaque medium, such as covered by walls or buried in the ground. Such compounds are of interest in the search for contraband, such as narcotics or explosives. In particular the chemical state of Nitrogen ($^{14}N$) is detectable by NQR and has a NQR frequency response signature that uniquely indicates many such compounds.

However, current NQR techniques are plagued by several problems. Increased penetration of a medium in which the target material is hidden involves lower frequencies that require a larger antenna or greater power inefficiencies. Also, the antennas suffer from loading effects by water in the medium and by any nearby broadcasting antenna. The above problems are shared by ground penetrating radar (GPR) as well. Furthermore, NQR suffers from the added complication of listening on a receiving antenna for a frequency signature with a power level that is orders of magnitude below the power level of the interrogating electromagnetic pulse emitted by a transmitting antenna. To accommodate the low return power, many current NQR systems use bulky and expensive detectors, such as a superconducting quantum interference device (SQUID), or use processing steps, such as pulse sequencing and background subtraction, to enhance a weak return signal.

SUMMARY

Techniques are provided for enhanced nuclear quadrupole resonance measurement and ground penetrating radar using metamaterial antenna A metamaterial is a device that expresses desired electromagnetic or physical properties that are not available from known materials. A metamaterial is an assembly of multiple individual microscopic structural elements fashioned from conventional materials such as metals or dielectrics, but the structural elements are usually arranged in periodic patterns. A metamaterial achieves one or more desired effects on propagating waves by incorporating structural elements of sub-wavelength sizes, i.e., with one or more features that are smaller than the wavelength of the waves affected.

In a first set of embodiments, a system includes a plurality of metamaterial antennae configured to both transmit and receive a corresponding plurality of magnetic fields focused at a corresponding plurality of near-field distances separated from the plurality of antennae, at a corresponding plurality of different antenna frequencies corresponding to a plurality of nuclear quadrupole resonance frequencies of an atom in a target material.

In some embodiments of the first set, the metamaterial antennae are configured to substantively eliminate de-tuning from loading effects from a nearby broadcasting antenna or water in a medium within the near-field distance of the metamaterial antennae.

In some embodiments of the first set, the system also includes at least one metamaterial lens disposed between the metamaterial antennae and a subject that might include the target material. The at least one metamaterial lens is configured to amplify focused near-field energy of an individual antenna frequency corresponding to a weak nuclear quadrupole resonance frequency or increase a corresponding antenna near-field distance to focus, or both.

In a second set of embodiments, a method includes interrogating a region of interest (ROI) with a ground penetrating radar (GPR) antenna to detect a suspect target material in a vicinity of the GPR antenna. The method also includes transmitting a plurality of nuclear quadrupole resonance (NQR) frequencies from a plurality of stacked metamaterial antennae focused at the suspect target material, and receiving, by the plurality of stacked metamaterial antennas, magnetic fields of NQR frequency signals from the suspect target material to capture a NQR frequency spectrum. The method further includes identifying, by a processor, the suspect target material based on the captured NQR frequency spectrum.

In a third set of embodiments, a system includes a metamaterial antenna configured to both transmit and receive a magnetic field focused at a near-field distance separated from the antenna at a corresponding antenna frequency corresponding to a nuclear quadrupole resonance frequency of an atom in a target material.

Still other aspects, features, and advantages of various embodiments are readily apparent from the following detailed description, simply by illustrating a number of particular embodiments and implementations, including the best mode contemplated. Other and different embodiments are anticipated, and their several details can be modified in various obvious respects, all without departing from the spirit and scope of the various embodiments. Accordingly, the drawings and description are to be regarded as illustrative in nature, and not as restrictive.

BRIEF DESCRIPTION OF THE DRAWINGS

The embodiments are illustrated by way of example, and not by way of limitation, in the figures of the accompanying drawings and in which like reference numerals refer to similar elements and in which:

FIG. 1D is a block diagram that illustrates a perspective view of an example artificial transmission line as part of an example metamaterial antenna, according to an embodiment;

FIG. 1E is a block diagram that illustrates an elevation view of an example metamaterial antenna, according to an embodiment;

FIG. 4A is a block diagram that illustrates an example system for enhanced NQR and GPR, according to one embodiment;

FIG. 5 is a flow chart that illustrates an example method for enhanced NQR and GPR, according to one embodiment;

FIG. 7A and FIG. 7B are graphs that illustrate example depth penetration of a metamaterial antenna, with and without a metamaterial lens, according to various embodiments;

FIG. 9 is a set of aligned graphs that illustrates example resonances of $^{14}N$ in various target materials and corresponding metamaterial antennae resonances for identification, according to various embodiments;

DETAILED DESCRIPTION

Figures 1A, 1B, 1C:
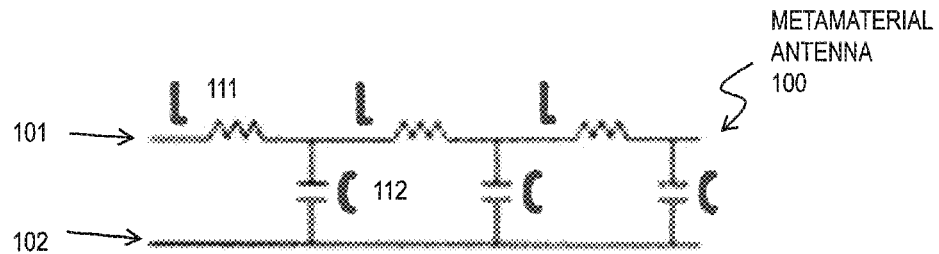
FIG. 1A is a block diagram that illustrates example structures for a metamaterial antenna, according to one embodiment.
FIG. 1B and FIG. 1C are example equations that illustrate the effect of the structures depicted in FIG. 1A, according to an embodiment.

A method and system are described for enhanced NQR and GPR. In the following description, for the purposes of explanation, numerous specific details are set forth in order to provide a thorough understanding of the various embodiments. It will be apparent, however, to one skilled in the art that various embodiments may be practiced without these specific details. In other instances, well-known structures and devices are shown in block diagram form in order to avoid unnecessarily obscuring the present invention.

Some embodiments are described below in the context of detecting and identifying buried explosives based on NQR of Nitrogen 14 ($^{14}N$). However, the various embodiments are not limited to this context. In other embodiments other materials hidden in other media are detected using different frequencies for mapping reflecting surfaces and different NQR frequencies of the same or different atoms in different target materials, such as buried narcotics or labeled or diseased tissue, in the same or different media, such as the human body, or cargo in a vehicle.

1. Principles

This section is provided to help explain the disclosed embodiments. However, the scope of the claims is not limited by the completeness or accuracy of this description of theoretical principles. The elementary particles, neutrons and protons, composing an atomic nucleus, have the intrinsic quantum mechanical property of spin. The overall spin of the nucleus is determined by the spin quantum number I. If the number of both the protons and neutrons in a given isotope are even, then I=0. In other cases, however, the overall spin is nonzero. A non-zero spin is associated with a non-zero magnetic moment, μ, as given by Equation 1a:

$$\mu = \gamma I \qquad (1a)$$

where the proportionality constant, γ, is the gyromagnetic ratio. It is this magnetic moment that is exploited in NMR. For example, nuclei that have a spin of one-half, like Hydrogen nuclei ($^{1}H$), a single proton, have two possible spin states (also referred to as up and down, respectively). The energies of these states are the same. Hence the populations of the two states (i.e. number of atoms in the two states) will be approximately equal at thermal equilibrium. If a nucleus is placed in a magnetic field, however, the interaction between the nuclear magnetic moment and the external magnetic field means the two states no longer have the same energy. The energy level is said to "split." The energy difference between the two states is given by Equation 1b:

$$\Delta E = \hbar \gamma B_0 \qquad (1b)$$

where h is Plank's reduced constant. Resonant absorption will occur when electromagnetic radiation of the correct frequency to match this energy difference is applied. The energy of photons of electromagnetic radiation is given by Equation 2:

$$E = hf \qquad (2)$$

where f is the frequency of the electromagnetic radiation and h=2 πℏ. Thus, absorption will occur when the frequency is given by Equation 3:

$$f = \gamma B_0/(2\pi) \qquad (3)$$

The NMR frequency f is shifted by the 'shielding' effect of the surrounding electrons. In general, this electronic shielding reduces the magnetic field at the nucleus (which is what determines the NMR frequency). As a result, the energy gap is reduced, and the frequency required to achieve resonance is also reduced. This shift of the NMR frequency due to the chemical environment is called the chemical shift, and it explains why NMR is a direct probe of chemical structure.

Applying a short electromagnetic pulse in the radio frequency range to a set of nuclear spins simultaneously excites all the NMR transitions. In terms of the net magnetization vector, this corresponds to tilting the magnetization vector away from its equilibrium position (aligned along the external magnetic field, $B_0$). The out-of-equilibrium magnetization vector precesses about the external magnetic field at the NMR frequency of the spins. This oscillating magnetization induces a current in a nearby pickup coil acting as a radio frequency (RE) receiver, creating an electrical signal oscillating at the NMR frequency. A portion of this time domain signal (intensity vs. time) is known as the free induction decay (FID) and contains the sum of the NMR responses from all the excited spins. In order to obtain the frequency-domain NMR spectrum (intensity vs. frequency) for magnetic resonance spectroscopy (MRS) and MRS imaging (MRSI), this time-domain signal is Fourier transformed.

Nuclear quadrupole resonance (NQR) is based on observations of nuclear quadrupole splitting in the absence of a static magnetic field. The quadrupole moment is a measure of the ellipticity of the charge distribution in the nucleus. Nuclei with spin $\geq 1$, such as $^{14}N$, $^{17}O$, $^{35}Cl$ and $^{63}Cu$, have an electric quadrupole moment. The quantum energy states of such charge distributions are split by an electric field gradient, created by the electronic bonds in the local environment, e.g., in a compound or crystal. The quadrupole splitting can often be observed directly because an RF magnetic field of the appropriate frequency can cause transitions between the levels. When the nucleus falls back to its lower state, a photon at the same frequency is emitted and can be detected. Relaxation times indicate the rate at which a nucleus in the elevated state emits the radio frequency photon and returns to the lower energy state. Due to the unique dependence of these energy levels on the specific material (chemical compound or crystal), this process enables precise identification of materials based on their NQR response. That is, the NQR technique is chemically specific, and can accurately identify a substance that has an NQR response.

Due to symmetry, the shifts become averaged to zero in the liquid phase, so NQR spectra can only be measured for solids. Many NQR transition frequencies depend strongly upon temperature.

2. Overview

As asserted in the background section, above, applying NQR for remote (standoff) determination of materials hidden in a medium is challenging using previous technologies. Previous NQR approaches include pulse sequencing and background subtraction to buy back a weak NQR signal. These do not deal with the fundamental issues of detection at depth through water loaded media at standoff. These also suffer from potentially long interrogation times. Other NQR approaches involve more sensitive detection schemes (e.g., superconducting quantum interference devices [SQUIDs]), as an alternative to inductive coils since they directly sense magnetic fields rather than magnetic flux. These can have similar issues in terms of packaging needs for optimal performance and ability to detect at depth through difficult media, such as water loaded media.

It was found that a metamaterial antenna designed to produce a long wavelength radio frequency electromagnetic field from a small footprint antenna to enhance magnetic field strength in a near-field for direct magnetic imaging, also had advantages in focusing RE magnetic fields at depth while avoiding loading by both water laden media and other broadcasting antenna in the vicinity. These features have been adapted to enhance both NQR detection of target material in water-loaded media and also water-loaded media penetrating radar (WLMPR), an enhancement to GPR.

FIG. 1A is a block diagram that illustrates example structures for a metamaterial antenna, according to one embodiment. The antenna is constructed as an artificial transmission line (ATL) with designed inductance (L) 111 and capacitance (C) 112 per unit length, L 111 is a function of the radius of curvature of a coiled conductor and the proximity to another coiled conductor. C 112 is a property of the separation distance between conductors and the dielectric material disposed between them. The conductor, radius of curvature, dielectric and separation properties can be engineered to achieve any desired L 111 and C 112 per unit length of the conductor.

FIG. 1B and FIG. 1C are example equations that illustrate the effect of the structures depicted in FIG. 1A, according to an embodiment. The effect of L 111 and C 112 is to change the group velocity vg of oscillating charges through the conductor at a radio frequency (RF), and thus the wavelength in the antenna for a given RE frequency, as given by equation 121 in FIG. 1B, presented her as Equation 4a:

$$vg=1/(LeffCeff)^{1/2} \quad (4a)$$

where Leff and Ceff represent the overall inductance and capacitance of the ATL. By slowing the speed vg, a frequency of interest can be emitted by an antenna that is smaller than the wavelength of that frequency in the media outside the antenna. Leff and Ceff also determine the impedance Z of the antenna according to equation 122 in FIG. 1B, presented here as Equation 4(b):

$$Z=(Leff/Ceff) \quad (4b)$$

In some embodiments, the impedance Z is designed to match the impedance of a supply line carrying the driving radio frequency pulse to the antenna or carrying the received signal away. By matching impedance of the supply line (e.g., at 50 ohms), RF electromagnetic energy is transferred efficiently between the antenna and the supply line, without the need for additional circuitry to introduce impedance. Thus for any GPR frequency or NQR frequency of interest, a metamaterial antenna can be designed that is smaller than a loop antenna needed to project or detect the same frequency and that matches the supply line impedance without the need for additional circuitry or superconducting components that require bulky cryogenic equipment.

The metamaterial antenna can also be characterized by its effective material properties of magnetic permeability and electrical permittivity (μeff and εeff, respectively) given by the equations 123, 124 of FIG. 1C and presented here as Equations 5a and 5b respectively, when exposed as a receiving antenna load on an external electromagnetic field:

$$\nabla^2 E + \omega^2 \mu eff\ \varepsilon eff = 0 \quad (5a)$$

$$Zw=(\mu eff/\varepsilon eff)^{1/2} \quad (5b)$$

Metamaterials with simultaneously negative permittivity (εeff) and permeability (μeff), are commonly referred to as left-handed (LH) materials. LHMs are considered to be a more general model of composite right/left hand (CRLH) structures, which also include right-handed (RH) effects that occur naturally in practical LHMs. The antennas proposed here have a composite right/left-handed (CRLH) dispersion curve that shortens the wavelength of the antenna frequency and has effective impedance Z of about 50 ohms.

FIG. 1D is a block diagram that illustrates a perspective view of an example artificial transmission line 144 as part of an example metamaterial antenna 130, according to an embodiment. This embodiment uses a metamaterial antenna as described in U.S. patent application Ser. No. 13/967,583 entitled "Resonant Magnetic Ring Antenna," the entire contents of which are hereby incorporated by reference as if fully set forth herein, except for terminology that is inconsistent with that used herein. The coil on a first face of a dielectric substrate is a planar spiral ring made of copper. Although each turn of the spiral is approximately circular in the disclosed embodiment, in other embodiments, each turn can have a different shape, such as a regular or irregular polygonal shape of three or more sides. A matching coil is disposed on the opposite face of the dielectric substrate 140. The matched pair of coils and the intervening dielectric form the artificial transmission line 144. Each coil is connected to a different port of a two port transmission line 142, also called a feeder line or feed line. In some embodiments, at the end of the innermost coil the conductor is connected to the conductor on the opposite face. This arrangement is called a Magnetic Ring Antenna (MRA) in the cited reference, and hereinafter.

FIG. 1E is a block diagram that illustrates an elevation view of an example metamaterial antenna 130, according to an embodiment. The metamaterial antenna 130 is an MRA that includes first and second ring elements 132 and 134 of conductor 146, connected to opposing first and second sides 136 and 138, respectively, of a substrate 140. In the example embodiments shown, the first and second ring elements 132, 134 are layered onto opposing sides 136, 138, respectively, of the substrate 140 in a corresponding, adjacent location so as to form a capacitor along the entire length of the artificial transmission line. In example embodiments, the substrate 140 is a dielectric material. In other example embodiments, the substrate 140 is a high frequency circuit material. In still other example embodiments, the substrate 140 is a ceramic-filled polytetrafluoroethylene (PTFE) material, such as, for example, the R03010 substrate available from Rogers Corporation®. In example embodiments, the substrate 140 is homogeneous and exhibits strong anisotropic properties. The MRA 130 is driven by a radio frequency (RF) electromagnetic field from a source (not shown), or outputs to a RE receiver (not shown) through a feed line 142, e.g., a 50 ohm coaxial feed line.

The properties of the metamaterial antenna are determined by the conductor material (e.g., copper), the dielectric material (e.g., R03010), the thickness 148 of the dielectric material (e.g., 5 millimeters, mm, 1 mm=$10^{-3}$ the inner radius 156 and the outer radius 158 of the coils (e.g., 4.875 inches and about 5.75 inches, respectively), the number of turns (e.g., six in the illustrated embodiment) of the conductor 146, and the spacing 150 (e.g., about 0.06 inches or about 1.52 mm in example embodiments) between the conductors on the same face, which determines the width 154 of the conductor on each turn. In some embodiments, an aperture 152 is formed in the substrate 140 within the inner radius 156. In some embodiments, the substrate is cut away outside the outer radius 158.

Figure 1F:
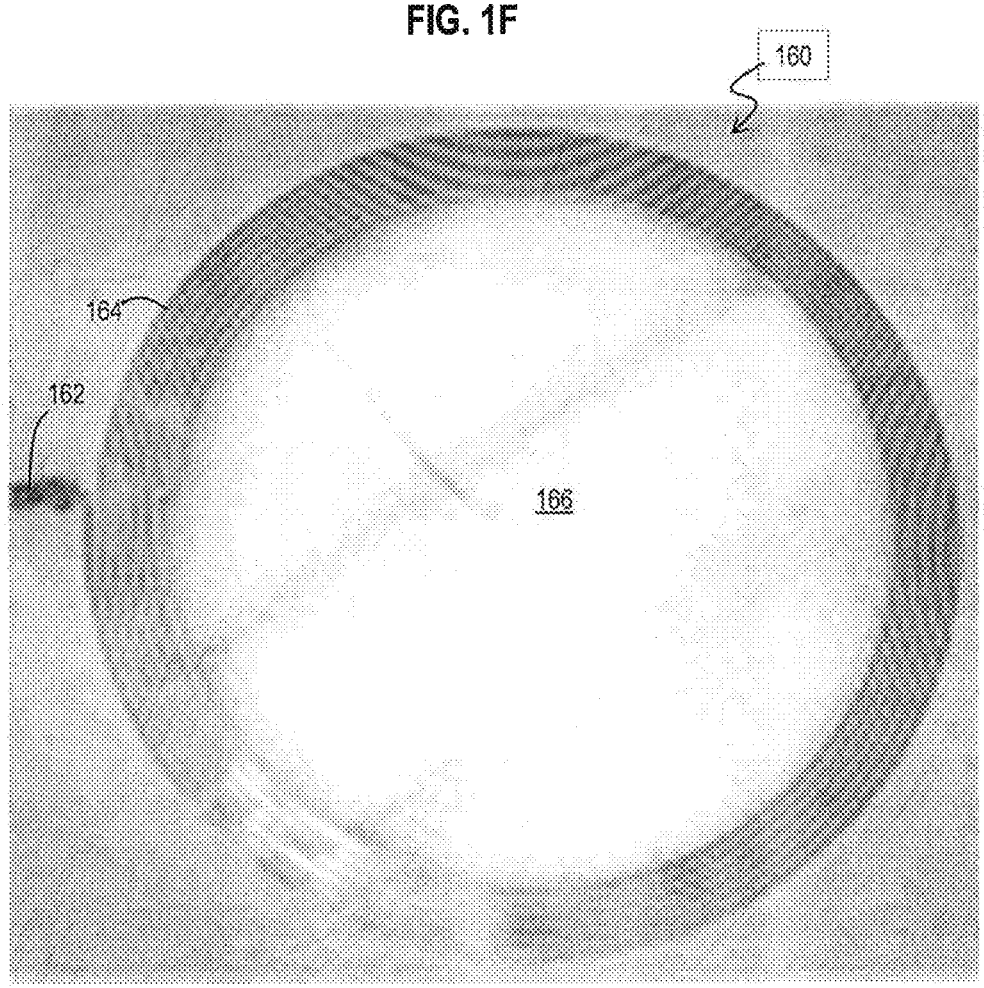
FIG. 1F is an image that illustrates a plan view of an example metamaterial antenna, according to an embodiment.

FIG. 1F is an image that illustrates a plan view of an example metamaterial antenna 160, according to an embodiment. Evident in FIG. 1F is the feed line 162, the substrate 166, and six turns of conductor 164 on one face of the substrate 166.

The MRA 130 shown and described herein has several advantageous aspects. A miniature antenna size using a simple transmission line (TL) approach and slow wave propagation behavior of magnetic waves in the metamaterial antenna can efficiently produce RF frequencies with propagating wavelengths much larger than the antenna. Furthermore, the antenna may be encoded to operate for a single resonant signal, and multiples thereof. In example embodiments, an MRA 130 is provided to operate at an effective impedance of 50 ohms near resonance, therefore requiring no external matching network.

Figure 1G:
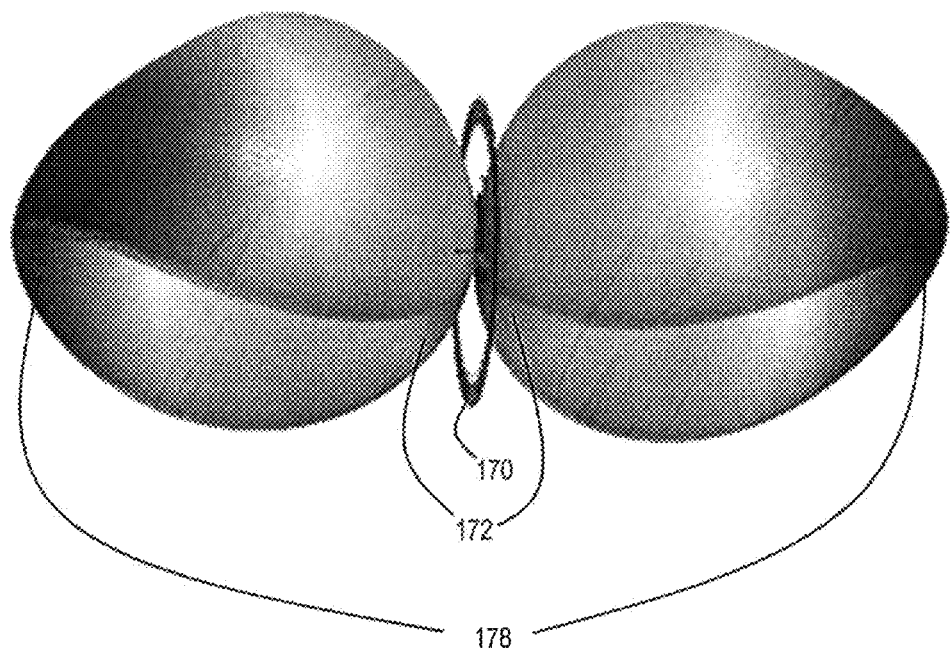
FIG. 1G is a graph that illustrates an example near-field E-field and H-field from a metamaterial antenna, according to an embodiment.

FIG. 1G is a graph that illustrates an example near-field E-field and H-field from a metamaterial antenna 170, according to an embodiment. The near-field (or near field) and far-field (or far field) are regions of the electromagnetic field around an object, such as a transmitting antenna. Non radiative 'near-field' behaviors of electromagnetic fields dominate close to the antenna, while electromagnetic radiation 'far-field' behaviors dominate at greater distances, more than a wavelength of the dominant frequency. Near-field behaviors decay rapidly with distance away from an object (e.g., on the order of the distance, D, cubed, $1/D^3$) whereas the far-field radiative field's intensity decays with an inverse square law ($1/D^2$). In the near-field, absorption of radiation affects the load on the transmitter. In the far-field, each part of the electromagnetic (EM) field is "produced by" (or associated with) a change in the other part. The ratio of electric to magnetic field strength is simply the speed of light. However, in the near-field, the electric and magnetic fields can exist independently of each other, and one type of field can dominate the other.

The dominant resonant frequency of an example 12 inch MRA 170 is 8.5 Megahertz (MHz, 1 MHz=$10^6$ Hertz, Hz, 1 Hz=1 cycle per second) which has a wavelength of 35 meters, much larger than the 0.3 meter size of the MRA. As depicted in FIG. 1G, for a metamaterial antenna 170 having characteristics of an MRA, both the electric field E and the magnetic field (H=E/377) diverges at first with large (in region 172) and then decreasing divergence, and then field lines converge with increasingly negative divergence and reach a focus in region 178 at a characteristic antenna near-field distance. Thus the antenna near-field measures the response to the field at the focus, the tip of the displayed field, at the near-field distance.

Figure 2:
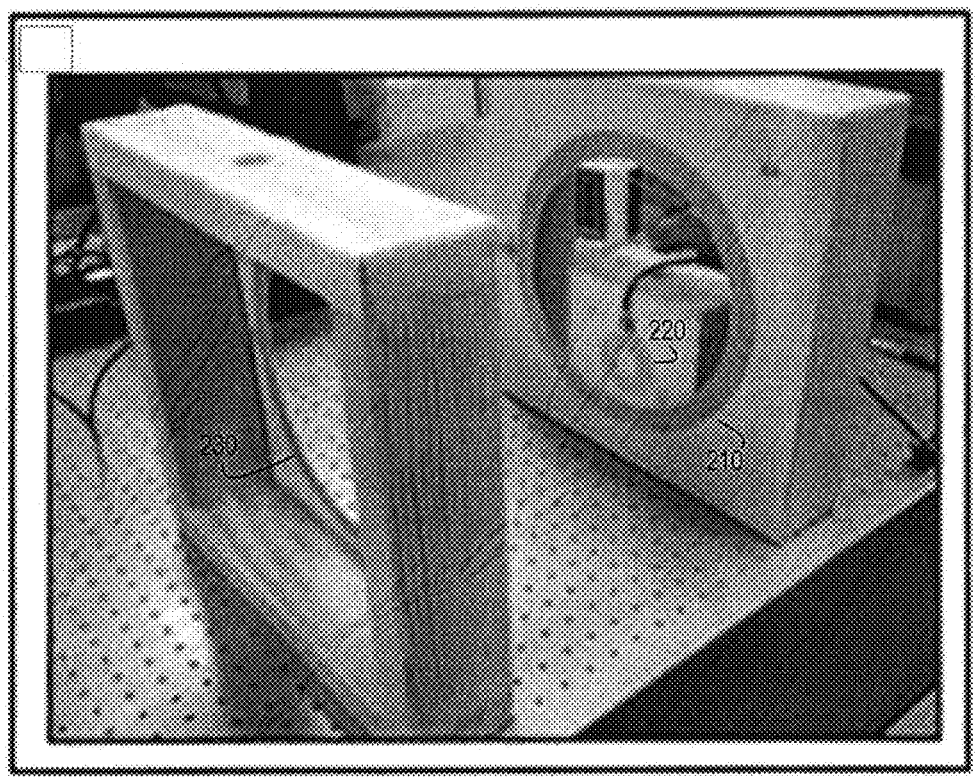
FIG. 2 is a photograph that illustrates an example of multiple layered metamaterial antennae, according to an embodiment.

It was discovered that the near-field produced by the MRA type metamaterial antenna did not interfere with (or "load") the near-field produced by a different MRA with a different set of resonant frequencies. This was demonstrated with an experimental setup depicted in FIG. 2 and described in more detail in a later section. FIG. 2 is a photograph that illustrates an example of multiple layered metamaterial antennae, according to an embodiment. Positioned within a 12 inch MRA 210, having a dominant resonant frequency at 8.5 MHz, is a three (3) inch MRA 220, having a dominant resonant frequency near 127.7 MHz. Both MRA were driven and produced fields at their respective resonant frequencies. The field at the resonant frequency of MRA 210 was received at receiving MRA 230 and did not show loading by the near-field of MRA 220.

It was further discovered, that both the far-field and the near-field of the MRA type metamaterial antenna did not show loading effects of water saturated media, as described in more detail below. Because the far-field also shows no substantive loading by water saturated media, such antennae are well suited for water-loaded media penetrating radar (WLMPR) applications, as well as GPR applications in general.

Thus it was realized, that metamaterial antennas, such as the MRA, are suitable for NQR detection of materials of interest hidden in a medium, for the following reasons. The metamaterial antenna can be tuned to frequencies that are characteristic of the target material and several such antenna can be used simultaneously to detect several frequencies that distinguish or uniquely identify a target material. This increases selectivity and reduces integration times over other systems. The maximum signal is induced at a standoff distance set by the antenna near-field distance so that the target material can be detected even if buried in the ground or walls or human body or other medium. The antenna distance is not adversely affected by water saturated media and so is effective in actual soil under real life conditions and in the human body. The built in transmission line impedance matching means that extra complexity and bulk and tuning is not required to match the impedance of the feed line. The increased signal strength at standoff means that more sensitive receiving antennas are not required and so complex, expensive, and bulky cryogenic superconductors like SQUID, are avoided.

In some embodiments, the metamaterial antenna is used in concert with a metamaterial lens to increase field strength and penetration distance. Any metamaterial lens with negative index of refraction or negative magnetic permeability is suitable. In the near-field, i.e. in the electro- or magneto static limit, the electric and magnetic fields can be decoupled and either or both permittivity $(\varepsilon)=-1$ or permeability $(\mu)=-1$ can be achieved, depending on whether electric or magnetic fields are of interest. Following Pendry's proposal, Fang et al. (N. Fang, H. Lee, C. Sun, and X. Zhang, "Sub-Diffraction-Limited Optical Imaging with a Silver Superlens," Science, Vol. 308, No. 5721, pp, 534-537, April 2005) used a silver slab as a superlens in the optical regime to image sub-wavelength electric sources. More recently, Freire et al. (M. J. Freire, R. Marques, and L. Jelinek, "Experimental Demonstration of a $\mu=-1$ Metamaterial Lens for Magnetic Resonance Imaging," Applied Physics Letters, Vol. 93, No. 23, pp. 231108/1-3, December 2008) designed a $\mu=-1$ metamaterial lens for a 1.5 Tesla (64 MHz) magnetic resonance imaging (MRI) system, using capacitively-loaded ring resonators. This metamaterial lens improved the signal to noise ratio (SNR) of the system and provided a sharp resolution, making such devices likely candidates for real-time MR imaging. Because metamaterials are based on sub-wavelength structures, the resolution of a metamaterial-based lens is limited by the size of its component resonators. Moreover, the loss of the material, the thickness of the lens, and the deviation of the effective material parameters from the ideal target of negative unity also limit the imaging performance. Most recently, an isotropic metamaterial lens with a negative unity permeability operating at 8.5 MHz for use in a 0.2 Tesla MRI system was developed here, and described in international patent application published as WO 2013/019883 entitled magnetic "Meta-Lenses for Magnetic Imaging," the entire contents of which are hereby incorporated by reference as if fully set forth herein, except for terminology that is inconsistent with that used herein.

Figure 3A:
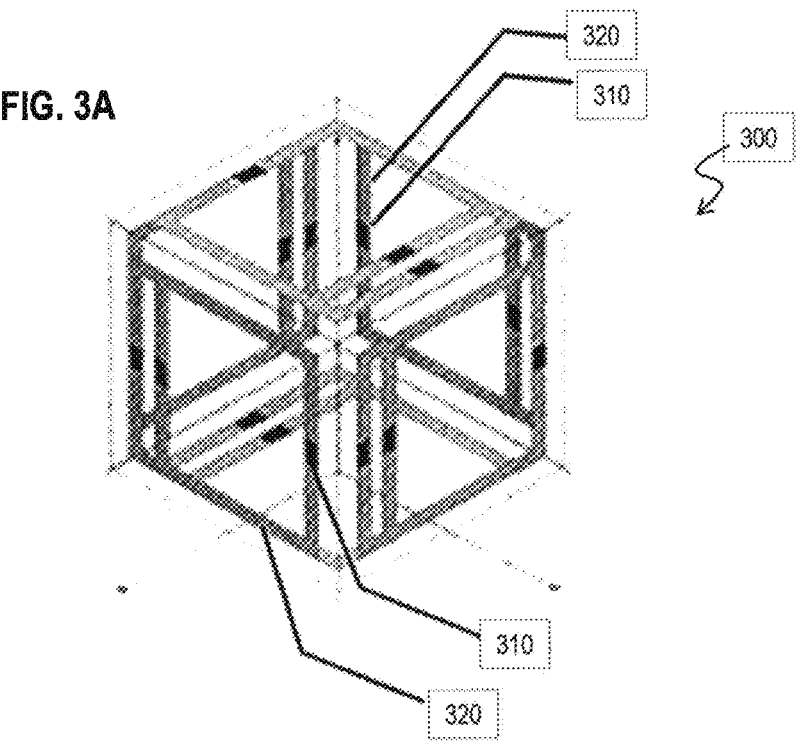
FIG. 3A is a block diagram that illustrates an example unit cell structure for a metamaterial lens, according to one embodiment.
Figure 3B:
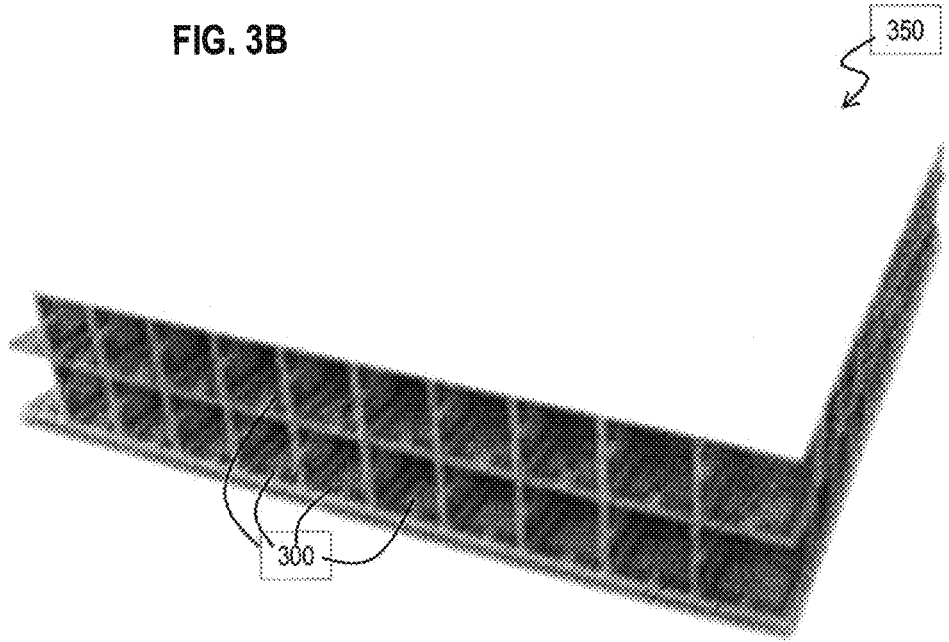
FIG. 3B is a block diagram that illustrates an example metamaterial lens, according to one embodiment.

In some embodiments, this last metamaterial lens is used. FIG. 3A is a block diagram that illustrates an example cube structure 300 for a metamaterial lens, according to one embodiment. Each face of the cube structure 300 comprises a conducting ring 320 with one or more capacitors 310. In some embodiments, as shown in FIG. 3A, the capacitors 310 on opposing rings 320 may alternate sides to eliminate or reduce bi-anisotropy. In some embodiments, such a capacitor-loaded conducting ring 320 may be printed on the inner wall of a dielectric on each side of the cube. FIG. 3B is a block diagram that illustrates an example metamaterial lens 350, according to one embodiment. Lens 350 is an example 3 dimensional (3D) periodic structure composed of such cube structures 300. A 3D periodic structure composed of such unit cube structures 300 has nearly identical responses to plane waves coming from three orthogonal directions.

FIG. 4A is a block diagram that illustrates an example system 400 for enhanced NQR and GPR, according to one embodiment. The system 400 includes multiple metamaterial antenna 410a, 410b, 410c (collectively referenced hereinafter as metamaterial antenna 410), such as MRA described above with reference to FIG. 1A through FIG. 1G, each designed for a different set of resonant frequencies associated with NQR for one or more atoms in a target material of interest. In other embodiments, more or fewer metamaterial antennae 410 are included in the system 400. Each metamaterial antenna is configured to both transmit and receive an electromagnetic (EM) field at an antenna frequency corresponding to a nuclear quadrupole resonance frequency of an atom in a target material. The transmitted and received EM fields focus a magnetic near-field at a corresponding antenna near-field distance separated from the corresponding antenna. The near-field patterns of the antennas 410a, 410b, 410c, among other represented by ellipsis, are depicted in FIG. 4A as electromagnetic (EM) near-field pattern 412a, 412b, 412c, respectively (collectively referenced hereinafter as near-field patterns 412). Although the near-field patterns 412 are shown while the system is operated for purposes of illustration, the near-field patterns are not part of the system 400 in a powered off state.

In some embodiments, the target material is contraband, such as narcotics or explosives. In some embodiments, the target material is a diseased or labeled tissue inside a human or animal body. In some embodiments, the atom is $^{14}N$ in a unique or distinguishing set of chemical states in the target material. The dominant NOR returns are from the dominant measurement area 490 where the antenna near-field distances of the respective antennae overlaps. Because the dominant measurement area 490 is displaced from the antennae 410 by the antenna near-field distance, the system 410 can be used in a standoff scenario, e.g., outside a surface 491 of medium 490 in which the target material, if present, is buried. Although the medium 490 and surface 491 are depicted for purposes of illustration, the medium 490 and surface 491 are not part of the system 400.

In the illustrated embodiment, the system 400 includes a metamaterial lens 420 tuned to focus at least one of the resonant frequencies of the metamaterial antenna 410. In some embodiments, more or fewer metamaterial lenses are included in the system 400.

In the illustrated embodiment, the metamaterial antennae 410 and any metamaterial lens 420 are held by a support structure 402, which secures the relative positions of the antennae 410 and lens 420.

Figure 10:
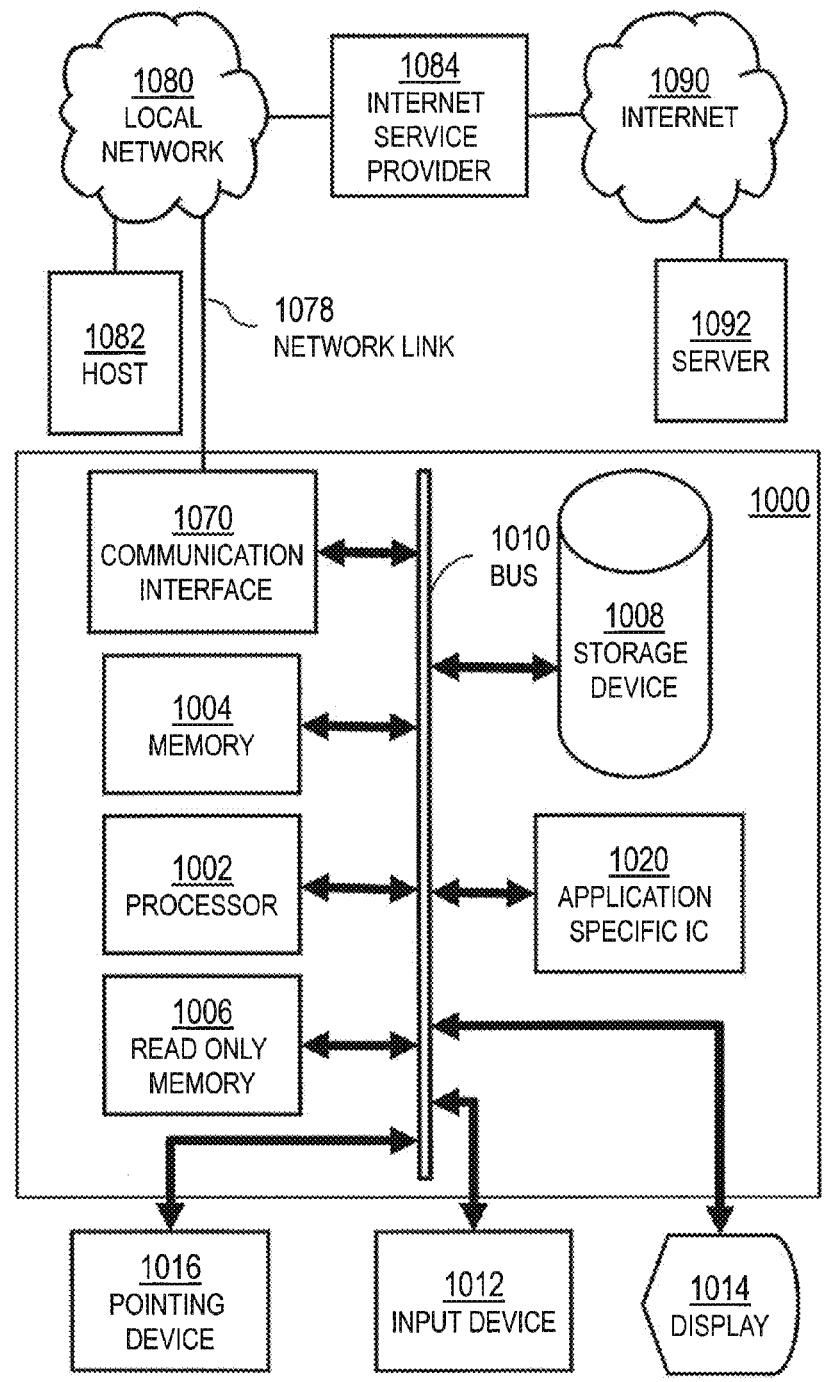
FIG. 10 is a block diagram that illustrates a computer system upon which an embodiment of the invention may be implemented.
Figure 11:
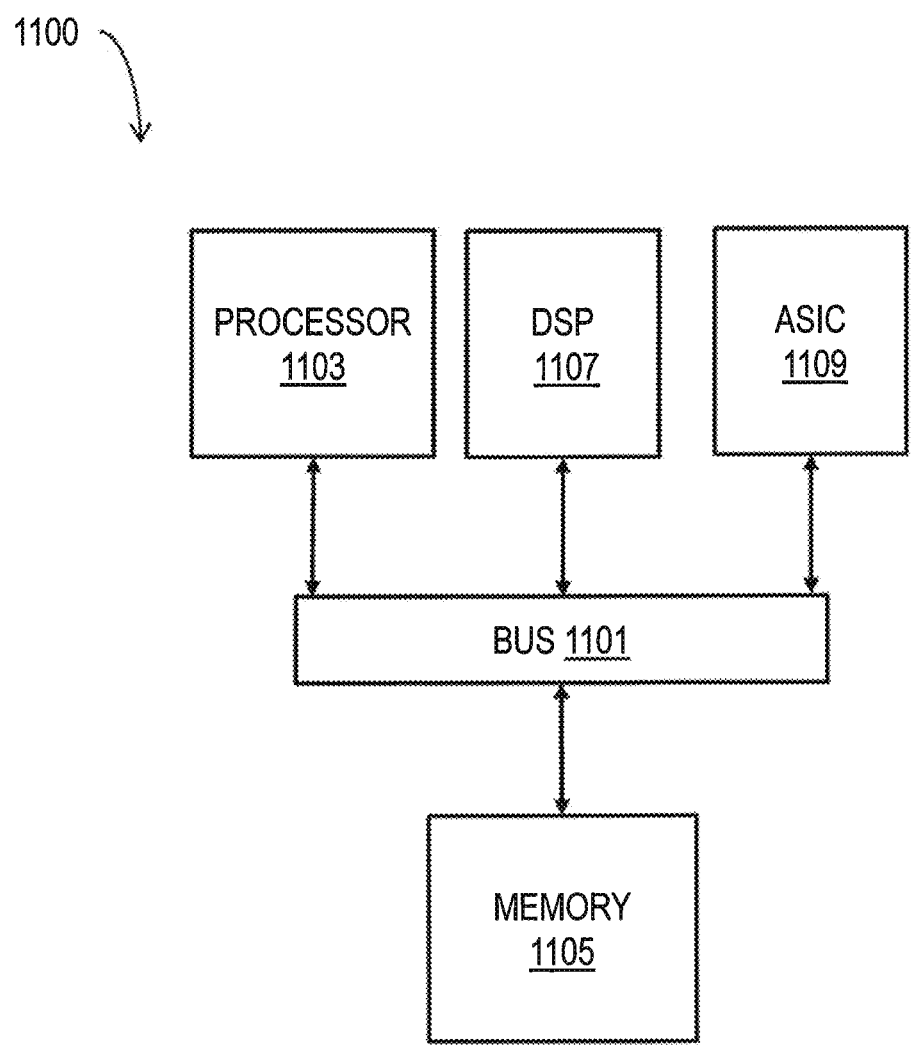
FIG. 11 illustrates a chip set upon which an embodiment of the invention may be implemented.

The system 400 includes analog driver/processor 450 that comprises analog circuitry that either supplies the RF electromagnetic signals through the feed lines 452 to drive each antenna 410, or receives the RF electromagnetic signals picked up the antenna 410 and fed through the feed lines 452 to an analog signal processor, or some combination. In some embodiments, the analog processor of driver/processor 450 determines the presence and the target material based on the signals received. In some embodiments, the system 400 includes a digital controller/processor 460 that interfaces with the analog circuitry, e.g., receives data based on the signals received from the antenna through an analog to digital converter or controls the activation of the antenna by the analog driver, or some combination. In some embodiments, the digital controller/processor is a computer system as depicted in FIG. 10 or chip set as depicted in FIG. 11 and described with reference to those figures. In some embodiments, the digital processor of controller/processor 460 determines the presence and the target material based on the data received. In some embodiments, a GPR function of detection or location of one or more reflection horizons, or both, from a propagating field from one or more of the antenna 410 is determined by one or more of the components 450 or 460 based on the returned signals received at the antenna 410 and fed through feed lines 452.

In some embodiments, the system 400 includes a user interface 470 that allows a user to determine when and what signals to emit from the antennae 410 and to notify the user of the presence of the target material. In some embodiments, the user interface 470 is part of digital controller/processor 460 or analog driver/processor 450. In the illustrated embodiment, the user interface is a separate device in wireless communication with the controller/processor 460 or driver/processor 450, such as a smart cellular telephone (smart phone). In various embodiments, one or more of the analog driver/processor 450 or digital controller/processor 460 or user interface device 470 are attached to the support structure 402.

Although components and processors are depicted in FIG. 4A, as integral blocks in a particular order for purposes of illustration, in other embodiments, one or more components or processors, or portions thereof, are arranged in a different order, or dissected or combined, or omitted, or other components are added, or the system is changed in some combination of ways.

Figure 4B:
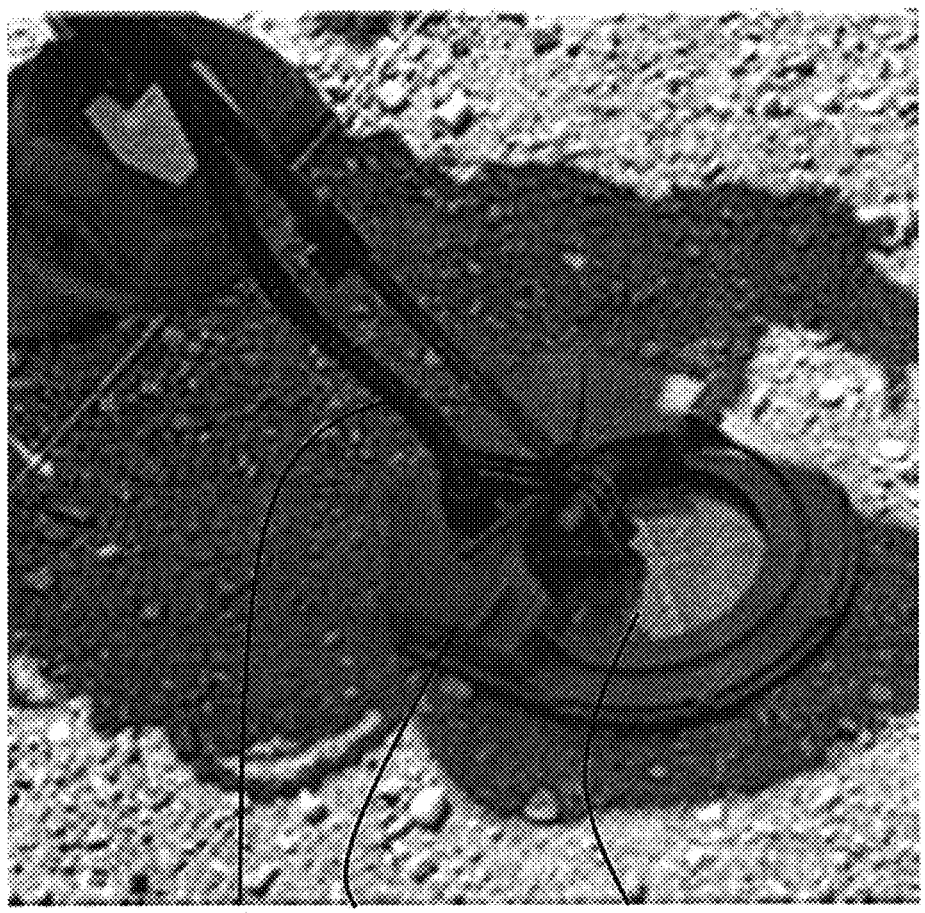
FIG. 4B is a photograph that illustrates an example appearance for a system for enhanced NQR and GPR, according to one embodiment.

FIG. 4B is a photograph that illustrates an example appearance for a system for enhanced NQR and GPR, according to one embodiment. The support structure 482 secures one or more metamaterial antennae 484 and passes one or more feed lines through a flexible conduit 486.

FIG. 5 is a flow chart that illustrates an example method 500 for enhanced NQR and GPR, according to one embodiment. Although steps are depicted in FIG. 5 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. For example, the system 400 is used with method 500.

In step 503, at least one antenna of the system is operated as a ground penetrating radar to interrogate a region of interest (ROI) to detect a suspect target material (e.g., explosive or narcotic). The GPR utilizes the electric near-field or propagating electric far field or both. For example, an area is quickly swept to detect reflectors using the propagating field of one or more of the antenna. The reflectors are indicative of buried objects or other changes in the medium. In some embodiments, the antenna is used for which the metamaterial lens is tuned to get the best penetration and most powerful reflections. In some embodiments, the shortest wavelength is used to find the reflectors closest to the surface with the greatest resolution. GPR systems are useful in the 1 MHz to 1000 MHz range, so in some embodiments, an MRA antenna, or a metamaterial antenna with a metamaterial lens, operates in one or more frequencies in this range. In some embodiments, GPR is not used and step 503 is omitted.

In step 505 the system is positioned based on the results of the GPR operation. For example, the system is positioned over a reflection indicative of a cavity where contraband could be stored or over a reflection characteristic of a shallow or deep buried improvised explosive device (IED). In some embodiments steps 503 and 505 are omitted, and no GPR precedes the NQR detection. The GPR horizon may contain no material of interest at all (e.g., it may be an empty cavity), or it may contain one or more materials of interest, which, if detected, are furthermore identified based on the received NQR spectrum.

In step 507, one or more of the antenna are configured for NQR detection and identification. The antennae are driven (used for transmitting) for which the resonant frequencies correspond to NQR frequencies that uniquely identifies or distinguishes the target material. The one or more antennae are driven for a duration sufficient to move the population of quadrupole nuclei to a more energetic state. The driving is done so that the dominant measurement area is in the vicinity of any suspicious reflective surface found during any GPR operations of step 503 and 505. At the end of step 507 the driving stops, and the one or more antenna stop emitting the EM field.

In step 509, received signals at the resonant frequencies of the one or more antennae are collected and processed, (i.e., the antennae are used for receiving). For example, the time domain signal received by an antenna with multiple resonant frequencies are Fourier transformed to determine which resonant frequencies are energetic and thus indicate the chemical environments of one or more quadrupole nuclei.

In step 511, the target material is identified based on the NQR frequencies detected. For example, step 511 is performed by analog processor 450 or digital processor 460 or user interface device 470, or some combination. If no target material is detected, the object is cleared. Otherwise, in some embodiments, the target material is identified based on its NQR spectrum, e.g., based on returns from two or more NQR frequencies. That is the target material is identified (which explosive, what narcotic, which cargo, etc.) based on the received signals and comparison to known signatures or spectra of the target materials.

Embodiments based on the above system and method directly addresses the pitfalls of conventional NQR systems through revolutionary, innovative hardware that substantively eliminates de-tuning from the unwanted loading effects of traditional antennas, provides the ability to engineer multiple resonances into each MRA in a small form factor, and the ability to enhance magnetic fields at depths in media that overcome the traditional $1/D^3$ decay of RF fields from traditional antennae.

3. Example Embodiments

Specific data have been obtained for several experimental and simulated embodiments, demonstrating the operation and usefulness of the system 400 and method 500 for the detection of various explosives. The metamaterial antenna used in these demonstrations involves either a twelve inch 8.5 MHz resonant MRA or a three inch 127.7 MHz resonant MRA, or some combination. The 12-inch MRA operates at resonant frequencies of 8.5 MHz and higher, while the 3-inch MRA operates at 127.7 MHz and higher. Several variants of permeability ($\mu$)=−1 metamaterial lenses for operation at 8.5 and 127.7 MHz have also been designed and fabricated. To demonstrate no substantive loading, some experiments or simulations involve a conventional solenoid broadcasting antenna and a vessel of water.

Improvised explosive devices (IEDs) are a persistent and continuing threat even as the theater changes from active engaged combat to peace missions. IEDs are currently the leading cause of death and injury for ground troops and a major factor in subsequent incidences of traumatic brain injury (TBI). IEDs can be found in multiple forms and may be hidden from their intended target in many ways. Many challenges exist with locating and identifying IEDs as adversaries adapt to current methods of fielded detection techniques: metal detection and/or ground penetrating radar (GPR). Many new IEDs have zero to little metal content and remain hidden to metal detectors.

With GPR, most systems operate at higher frequencies (>500 MHz). Two major issues arise with GPR. First, the penetration depth through soil generally scales with frequency—lower frequencies have better depth penetration through most embedding media of interest. Second, conventional antenna theory requires a larger aperture antenna to achieve an efficient output signal for a larger wavelength. The consequence of this is that a lower frequency antenna has to be much larger or else use more energy (but with much more inefficiency). Also, these lower frequency antennas are plagued by loading effects from water and other nearby and broadcasting antennas used in the set up. This then requires a whole host of controlling electronics and calibration techniques that can drop the fidelity in locating and identification of an IED.

In spite of some of the issues in using GPR, it is still a technique that is currently fielded, for dismounted systems (e.g., handheld systems) to check for landmines and other potential IEDs. This is likely due to the fact that it is one of the few sensor technologies for detection of a buried, disturbance that can be made into a hand held or portable system and perform some type of "imaging" function. Some of the antenna characteristics that are desirable to GPR are broadband radiation characteristics, compact, low dispersion, and a minimal radar cross section. The minimal radar cross section helps reduce multiple reflections between the antenna and the ground surface.

Example $^{14}$N NQR frequencies range between low kilohertz (kHz, 1 kHz=$10^3$ Hertz) to 6 MHz. When interrogating a sample, a signature response from a material with energetically bonded $^{14}$N will be emitted anywhere in this range depending on the explosive. A great advantage of NQR is that while it is the $^{14}$N nuclei being interrogated, due to its local environment each explosive will have one or more NQR signals that do not overlap with any other explosive's NQR signal. There are various known explosives that could be used in an IED (e.g., HMX, RDX, TNT, forms of ammonium nitrate or urea nitrate, etc.). The return times on the NQR signal and the ability to acquire them depend on the relaxation times T1 and T2. The relaxation times indicate how long a population takes to leave an excited state or return to a ground state from an energized state and, thus, determines how rapidly a pulse sequence can be repeated. Some relaxation time bounds the maximum length of the spin echo used for detection. These are often short (less than about a millisecond, ms, 1 ms=$10^{-3}$ seconds), but can make fast acquisition difficult especially when trying to identify multiple explosive compound with statistical confidence by many repeated measurements and making serial measurements at different frequencies.

Due to the operation frequencies, state-of-the-art (SOA) NQR techniques are plagued by the same technical issues as low frequency GPR, but with the added complication of listening for a frequency signature that is orders of magnitude below the input interrogating power, as described above. As indicate in the background section, current SOA NQR approaches include pulse sequencing and background subtraction to buy back a weak NQR signal. These do not deal with the fundamental issues of detection at depth through opaque media or at standoff. These also suffer from potentially long interrogation times. Other NQR approaches, in terms of detection schemes (i.e., superconducting quantum interference devices [SQUIDs]), have also been used as an alternative to inductive coils since they directly sense magnetic fields rather than magnetic flux. These can have similar issues in terms of packaging needs for optimal performance and ability to detect at depth.

Using the metamaterial-based antenna miniaturization technique described above, a 12-inch (0.3 m) diameter, 0.010 inch (0.25 millimeter (mm, 1 mm=$10^{-3}$ meters) thick, non-superconducting resonant antenna at 8.5 MHz with wavelength ($\lambda$)=117.65 feet (35.86 m) has been constructed. This embodiment uses R03010 substrate in a ring with an inner radius of 4.75 inches (about 121 mm) and an outer radius of 5.75 inches (about 146 mm), on both sides of which is deposited copper spiral rings with inner diameter 156 of 4.875 inches (about 124 mm), with six turns and spacing 150 of 0.06 inches (about 1.5 mm) and pictured in FIG. 1F. Also constructed was a 9-inch (0.23 m) diameter, 0.010 inch (0.25 mm) thick, non-superconducting resonant antenna at 127.7 MHz with wavelength ($\lambda$)=7.83 feet (2.39 m).

This MRA does not change performance with use of other nearby or broadcasting antennas, or when in direct contact with water-loaded media, as demonstrated below. For a GPR component in some embodiments, the same design methodology is used to derive the antenna though it may or may not necessarily be an MRA. In some embodiments, a negative permeability ($\mu$=−1) metamaterial lens, such as described above with reference to FIG. 3A and FIG. 3B, is used, which enhances the near field of an RF magnetic field, even at depth. Analysis on the anticipated enhancements from incorporation of such meta-lenses for these techniques is included. Much of the data presented here includes experimental data involving both the MRAs and metamaterial lens to give an appreciation of the potential enhancements for the GPR and NQR sensor performance.

An advantage of these embodiments is that there is no need for much of the controlling electronics or hardware isolators that are currently used in conventional systems. This means the operation of the novel system is independent of the media of interest or its co-location with other sensors. These metamaterial GPR or WSMPR antennas can be used to perform localization of a potentially hazardous anomaly and then the NQR resonant metamaterial antennas used to identify whether or not the anomaly is explosive in nature. One or more negative permeability ($\mu$t=−1) metamaterial lenses enhance the near-field of an RF magnetic field, even at depth, through different media.

Another benefit of some embodiments is that the example MRAs have multiple resonances, which can be engineered to occur at desired frequencies. For example, if a high explosive has 4 prominent spectral signatures below 6 MHz, an MRA can be engineered with resonances to accept one, two or more of those signature frequencies while rejecting many others. These resonances can be made broad enough to encompass normal temperature fluctuations expected in the operational environment of interest so that an NQR signal that is energetically shifted up or down around the main room temperature resonance will still be detected. This is an advantageous feature as it decreases the need for controlling electronics and filtering media. This implies such antenna are more directly "sensing" the threat and relying less on software to find the information. Also, because these MRAs do not interact with each other, multiple MRAs for multiple compounds can be included in close proximity to each other. Due to their small size, weight, and lack of need for a true isolator, some embodiments can do quick interrogation for several explosive compositions in parallel.

Typically, antennas with a low radiating resistance may raise concerns that most of the transmitted or received power is dissipated in loss resistance and produce inefficiency. Since atmosphere noise and man-made noise (~55 dB) dominate above thermal (Johnson) noise below 6 MHz, the low radiation resistance in the MRA design is not a concern. The MRA's electrical inefficiency has little impact on the receiving system's signal-to-noise ratio (SNR). Thus, the non-loading property of the MRAs constitutes a useful factor for meeting the needs associated with implementing NQR in a non-laboratory environment.

Antenna performance is often characterized by S parameters. S parameters describe the input-output relationship between ports (or terminals) in an electrical system like an antenna. A port can be loosely defined as any place where voltage and current can be delivered, such as a feed line 142. For two ports called Port 1 and Port 2, then S12 represents the power transferred from Port 2 to Port 1. S21 represents the power transferred from Port 1 to Port 2. In general, SNM represents the power transferred from Port M to Port N in a multi-port network. So S11 is then the reflected part of the power feeder line 1 is trying to deliver to antenna 1 (which is minimized if the antenna impedance matches the transmission line impedance). Power ratios are often expressed in decibels (dB), a logarithmic scale defined by Equation 4a for power and 4b for amplitude $$LdB=10\ log_{10}(P1/P0) \tag{4a}$$

where P0 is provided power and P1 is returned power and LdB is power ratio in deciBels; and $$LdB=20\ log_{10}(A1/A0) \tag{4b}$$

where A0 is provided amplitude and A1 is returned amplitude.

Figure 6A:
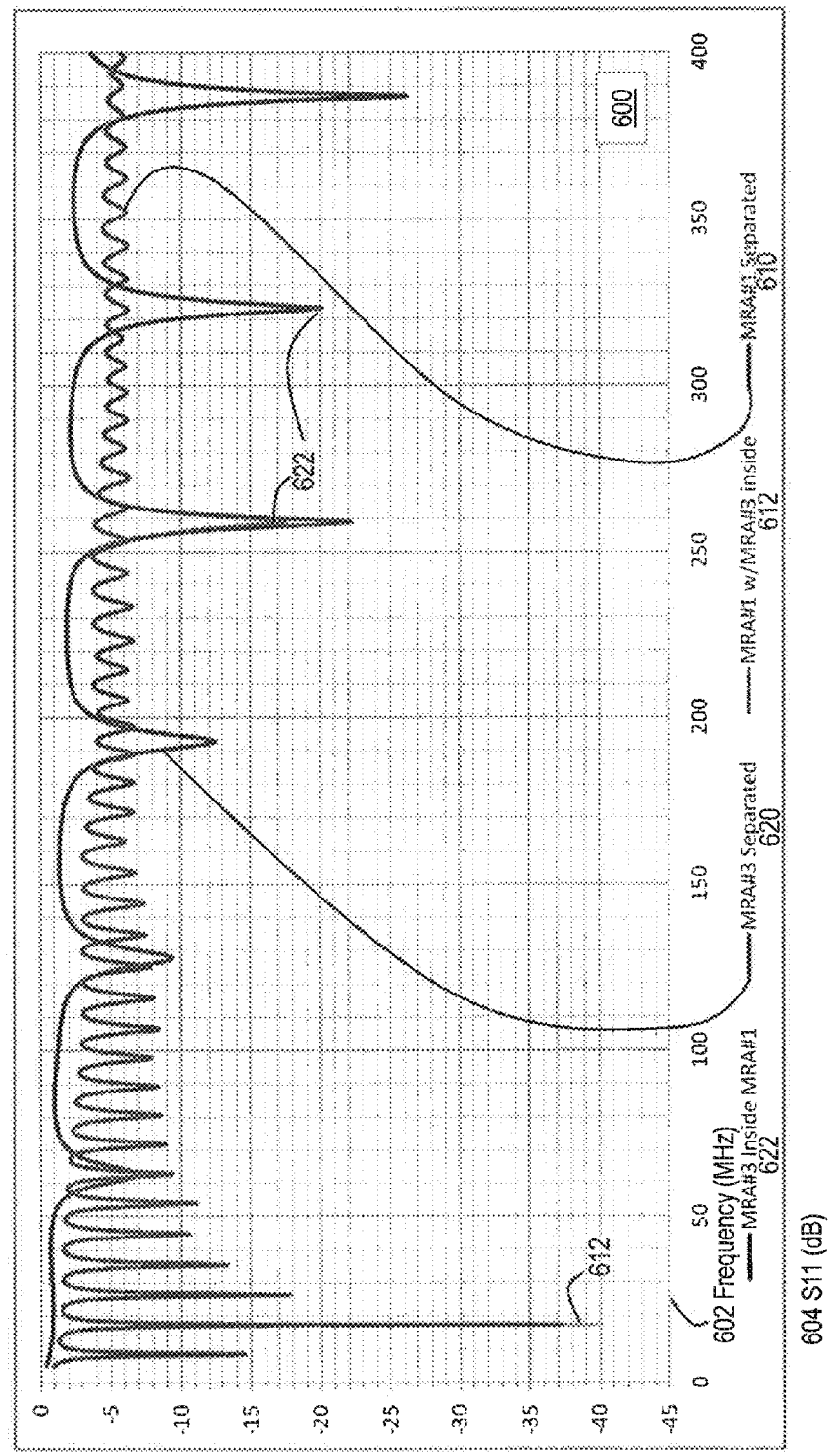
FIG. 6A and FIG. 6B are graphs that illustrate example radio frequency responses of two metamaterial antennae, which are the same when together or apart, according to various embodiments.
Figure 6B:
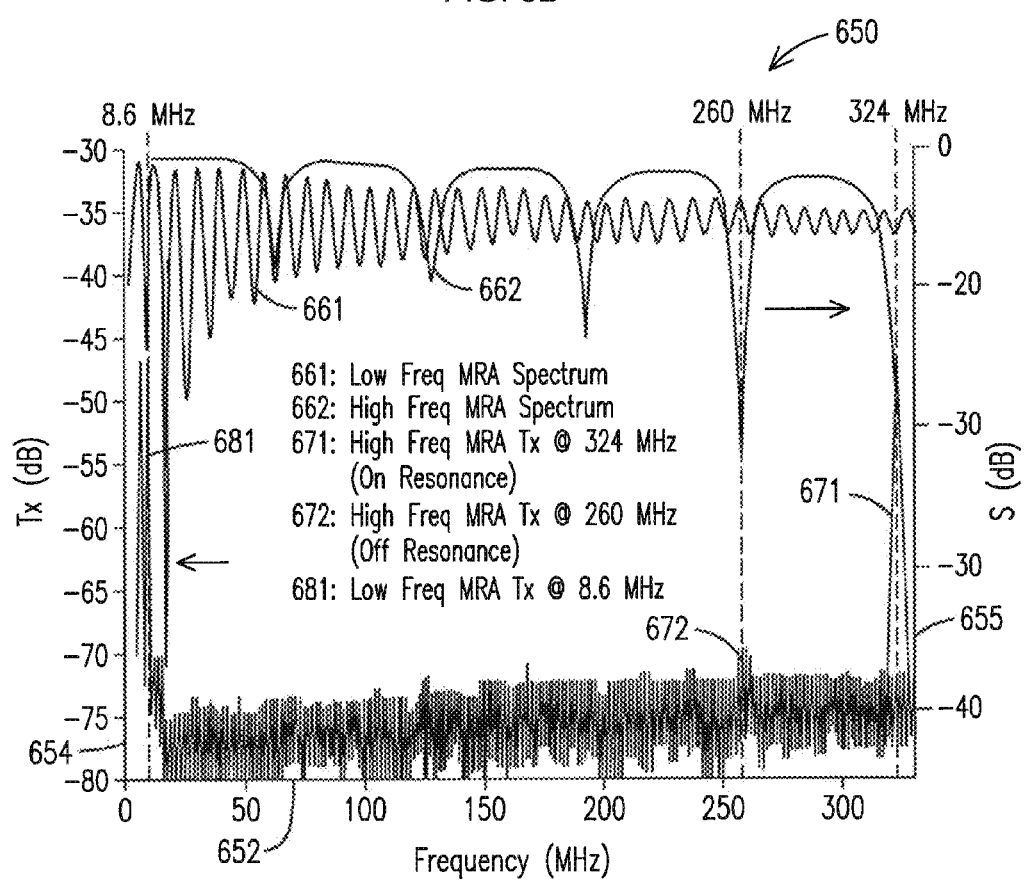

To test the independent operation of MRAs, two MRAs transmitting separately or simultaneously as depicted in FIG. 2 were tested. FIG. 6A and FIG. 6B are graphs that illustrate that example radio frequency responses of two metamaterial antennae are the same when together or apart, according to various embodiments. FIG. 6A is a graph 600 that indicates frequency in MHz on the horizontal axis 602 and S11 in dB on the vertical axis 604. Resonances are indicated by minima in the value of S11. Trace 610 indicates the resonant response of the low frequency (12 inch diameter) MRA#1, described above, operating alone (separately). Trace 610 shows resonances (minima in S11 values) at 8.5 MHz and multiples thereof. The strongest resonance is at about 17 MHz. Trace 620 indicates the resonant response of the high frequency (3 inch diameter) MRA#3, described above, operating alone (separately). Trace 620 shows resonances (minima in S11 values) at about 64 MHz and multiples thereof, including about 128 MHz (nominally 127.7 MHz), about 194 MHz, about 259 MHz, about 322 MHz and about 387 MHz. The strongest resonance is at about 387 MHz and next strongest at about 359 MHz.

These traces are not changed much by placing another MRA in the vicinity. For example, placing the high frequency antenna MRA#3 inside the low frequency antenna MRA#1, as depicted in FIG. 2, does not change the resonances of the low frequency antenna appreciably. The resonance in this case, given by trace 612, overlaps trace 610 except for a slightly lower value of S11 in trace 612 at about 18 MHz, a change of less than about 10%. Neither is the resonance structure of the high frequency antenna MRA#3 changed appreciably. The resonance in this case, given by trace 622 overlaps trace 620 except for a slightly lower value of S11 in trace 622 at about 322 MHz (less than 10% difference), and a slightly higher (less negative) value of S11 at about 259 MHz a change of about 10%. That is, there is not much loading of one antenna by the presence of other.

FIG. 6B is a graph 650 that illustrates example suppression of off resonant signals. Horizontal axis 652 indicates frequency in MHz; and, the vertical axis 654 indicates transmitted power (Tx) in dB, corresponding to S12. The traces 661 and 662 correspond to traces 610 and 620 depicted in FIG. 6A but placed at a displaced vertical position given by axis 655 in dB to indicate the resonant frequencies of the two metamaterial antenna used. The high frequency MRA (3-inch diameter MRA#3) was first set to transmit with the low frequency MRA (12-inch diameter MRA#1) acting as receiver. The result is shown as peak 671 that clearly depicts that the low frequency MRA receiver strongly receives the "on resonance" frequency at 324 MHz, while barely detecting the "off resonance" frequency at 260 MHz 672. The 260 MHz frequency does not match the resonance spectrum of the receiving MRA engineered resonance bands. This is truly different from any other known NQR architecture in that this gives the ability to do simultaneous interrogation at multiple NQR frequencies. It is believed that this multi-acquisition along with the improved NQR signal will improve the false positive/false negative rates because of the ability to improve SNR regardless of the medium and the ability to interrogate multiple NQR frequencies simultaneously. Similar results are fund for both antenna transmitting. With the second low frequency MRA (12 inch diameter MRA#2) acting as transmitter, the peak 281 at 8.6 MHz is clearly detected.

These are the results of tests with on-resonant and off-resonant frequencies simultaneously radiated to verify the robust properties of the MRA, and its ability to "reject" any signals not associated with an MRA resonance. This last property has two important features for NQR and also GPR. First, multiple antennas can be fabricated specific to more than one compound of interest, and used in a stacked configuration without performance impact. This may offer the ability to decrease the acquisition time due to the ability to pulse and collect multiple frequencies within one or more MRAs interrogating the same area of interest in parallel. In some embodiments, each antenna is operated independently with separate back end hardware. In some embodiments, at least one antenna is used with a different pulse sequence from at least one other antenna. In some embodiments, the return time is independently controlled for each spectral frequency of interest in of the plurality of NQR frequencies. In some embodiments, the antenna operation is configured to be silenced after a blast and then used in a next transmission after a predetermined relaxation time.

To test the depth dependent operation of MRAs, two dimensional (2D) scan profiles of the near-field pattern of an 8.5 MHz MRA confirms am converging (e.g., focusing or field concentration) behavior after distances of 2 inches from the MRA. In these 2D scans, a small 1-inch loop antenna was used to capture more of the magnetic field portion of the emitted field. The profiles indicate that the intensity profile as the field decays is unique in that it maintains a concentrated field profile even at long distances (12 inches). Many conventional resonant antennas express, at long distances, a field that diverges beyond the original aperture size of the antenna and has a faster decay rate than the MRA described herein.

An issue in bulk identification of an embedded IED or explosive in difficult media is the ability to get a sufficient RF field energy through that media to 1) detect the anomaly to using GPR and 2) to apply the proper force to the nucleus and get a sufficient NQR signal for positive identification. The stronger the RF field strength, the better the return signal, which is already weak in comparison to the interrogating field. In ideal scenarios (e.g., laboratory settings), the NQR return signal can be as high as an order of magnitude lower than the input power; but, depending on which energy level is being interrogated, this quadrupole phenomena (due to asymmetry) can degrade the return signal even further. Adding in the effects of distance means that the ability to obtain a good NQR signal is not trivial even though the physics are elegantly simple.

Figure 7A:
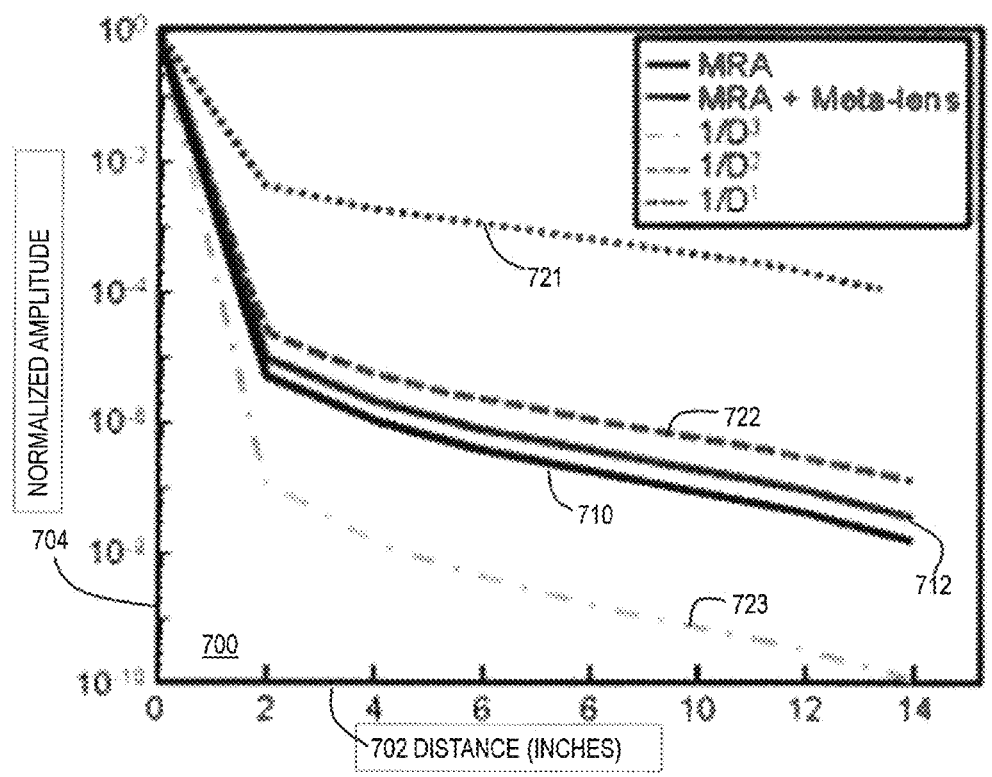

FIG. 7A and FIG. 7B are graphs that illustrate example depth penetration of a metamaterial antenna, with and without a metamaterial lens, according to various embodiments. FIG. 7A is a graph 700 that depicts measurements of near-field magnetic field with distance from an MRA antenna in free space. The horizontal axis 702 is distance in inches; the logarithmic vertical axis 704 is amplitude normalized to I at the antenna. Traces 721, 722, 723 show the values at the measurement points for a theoretical field falling off with the first power (1/D), square (1/D$^2$) and cube (1/D$^3$) of the distance D from the antenna. The near-field of a conventional, well radiating, resonant solenoid falls off as the cube of the distance as shown by trace 723. Trace 710 shows the measurement for the low frequency MRA (12 inch diameter) itself in free space. Trace 722 shows the measurements for the MRA coupled with a tuned metamaterial lens in free space. Both fall off much slower than 1/D$^3$, and much closer to 1/D$^2$.

It is noted that a decay rate at 1/D$^{2.5}$ at short distances will have approximately twice the energy as a field decaying at 1/D$^3$, while at longer distances this goes up to a three times increase in energy. FIG. 7A shows decay rates better than 1/D$^{2.5}$, allowing transmitting signals at much deeper penetration depths than with traditional solenoids. This MRA feature, coupled with its robust, non-loading properties, provides the valuable capability of enhancing the RE magnetic field to detect NQR signals at greater depths.

FIG. 7B is a graph 750 that depicts measurements of near field magnetic field in soil at depth. The horizontal axis is frequency in MHz; and, the vertical axis is amplitude in dB. Measurements are taken through 12 inches of dirt and one inch of free space. Trace 760 indicates amplitude from the low frequency MRA (12 inch diameter MRA#1) resonant at 8.5 MHz. Trace 762 indicates amplitudes from the same MRA coupled with the metamaterial lens of FIG. 2B. Trace 770 indicates measurements for a conventional, well radiating, resonant solenoid at 8.5 MHz In soil, the experimental embodiments outperform the well radiating resonant solenoid by about 5 to 8 dB at depths up to 12 inches for MRA and MRA with metamaterial lens, respectively. With optimization, there is the potential to perform even better.

Figure 8A:
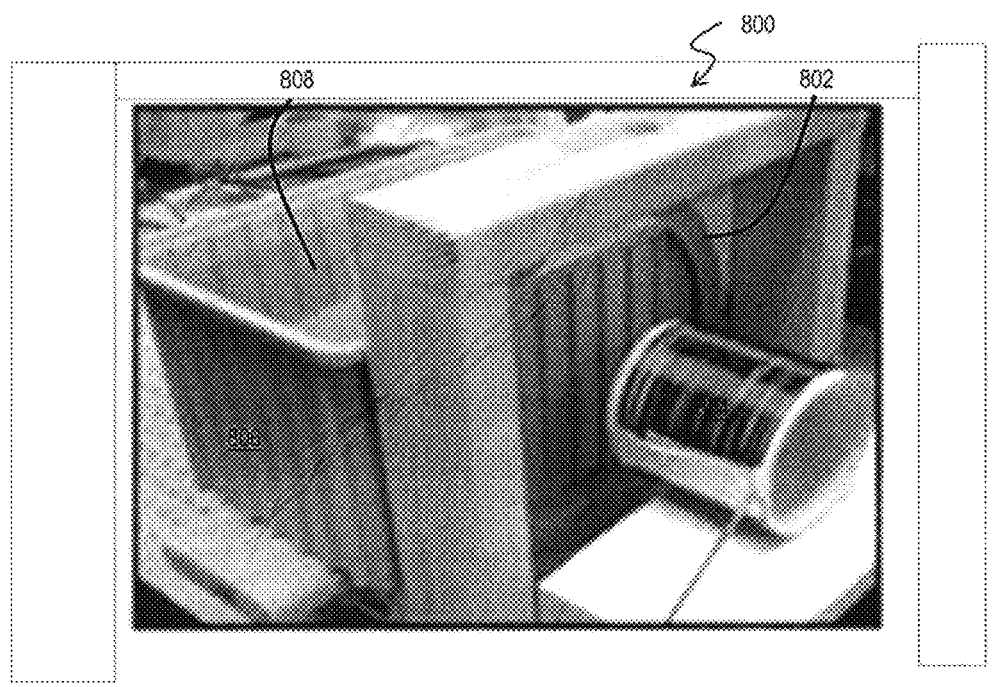
FIG. 8A is a photograph that illustrates an example experimental setup to measure loading by water in a medium and by a separate broadcasting antenna, according to an embodiment.

To test the dependence of MRA operation on water content in a medium hiding the target material, additional experimental embodiments were implemented. FIG. 8A is a photograph that illustrates an example experimental setup 800 to measure loading by water 808 in a medium and by a separate broadcasting antenna 804, according to an embodiment. The separate broadcasting antenna 804 is a conventional resonant solenoid. The water 808 is contained in vessel 806. The performance of the low frequency MRA 802 (12 inch diameter MRA#2) is determined.

Figure 8B:
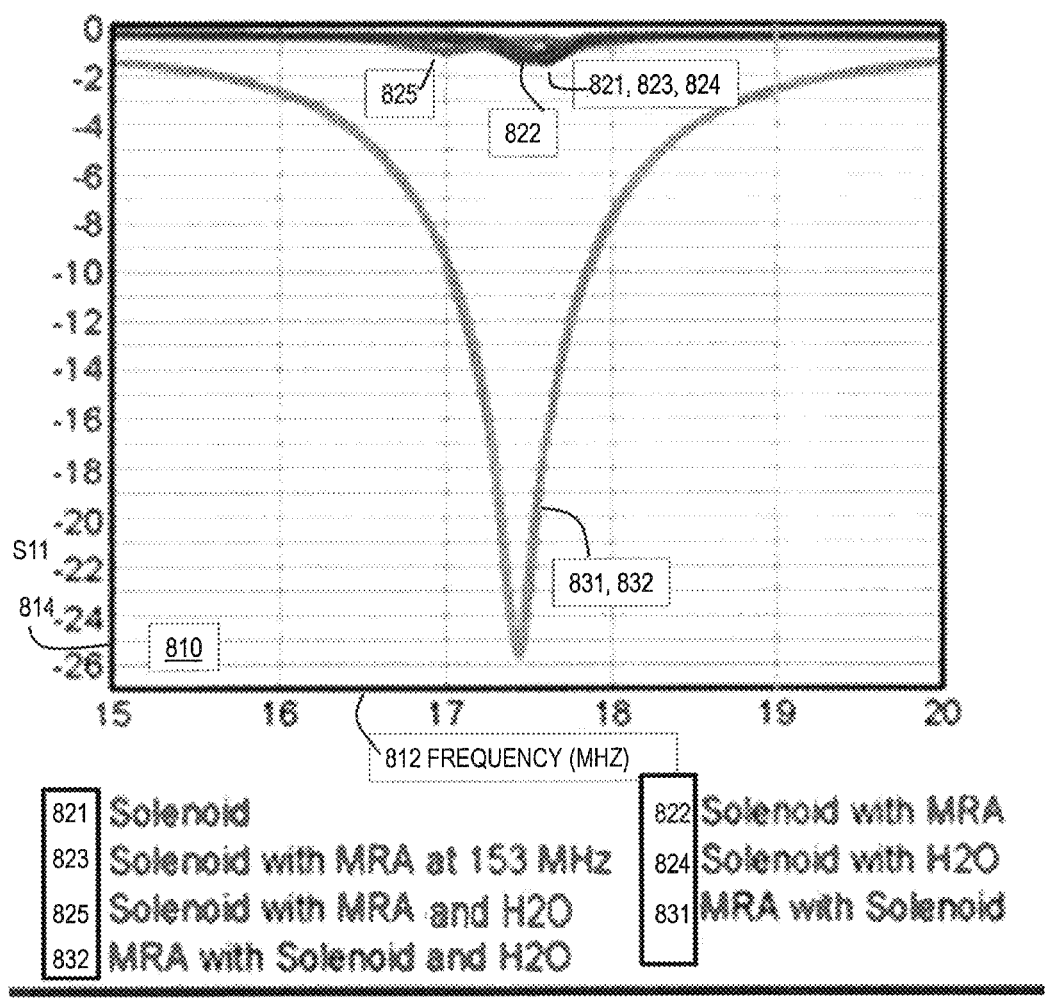
FIG. 8B and FIG. 8C are graphs that illustrate example minimal loading of a metamaterial antenna by water in a medium or a separate broadcasting antenna, according to various embodiments.
Figure 8C:
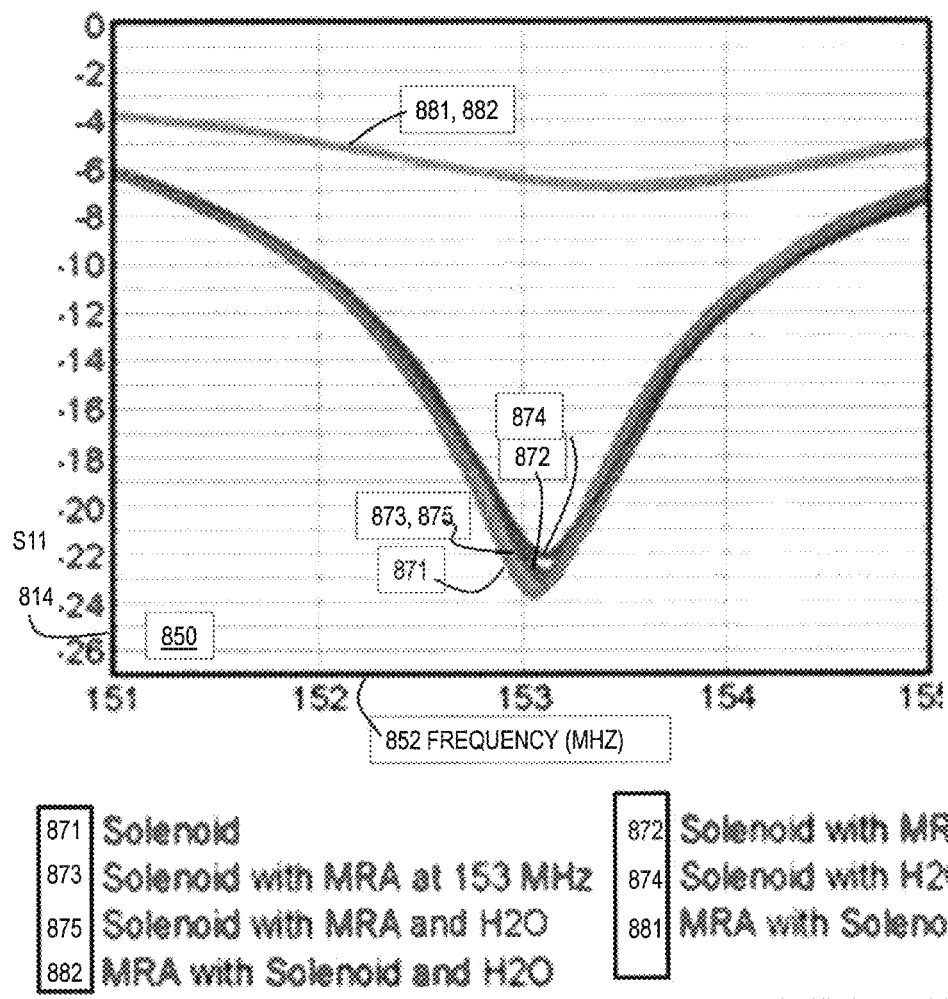

Two resonance bands at 17.5 MHz and 153 MHz were selected since both the MRA and solenoid show spectral features in these bands. FIG. 8B and FIG. 8C are graphs that illustrate example minimal loading of a metamaterial antenna by water in a medium or a separate broadcasting antenna, according to various embodiments. FIG. 8A is a graph 810 that illustrates example dependence in the vicinity of 17.7 MHz. The horizontal axis 812 indicates frequency in MHz; and vertical axis 814 indicates S11 in dB. The MRA has a deep resonance at 17.7 MHz even with the solenoid present, as indicated by trace 831; and, trace 831 is indistinguishable from trace 832 indicating the response for the MRA with solenoid and water. In contrast, there is little resonance at 17.7 MHz for the solenoid alone as indicated by trace 821. However little resonance there is, the resonance is substantively affected (e.g., on the order of 50% in power and more) by the presence of the MRA as indicated by trace 822 and by MRA and water indicated by trace 825. With water alone or a MRA at 153 MHz the traces 823 and 824, respectively, are very close to the solenoid alone trace 821.

FIG. 8C is a graph 850 that illustrates example dependence in the vicinity of 153 MHz. The horizontal axis 852 indicates frequency in MHz; and vertical axis 814 is the same as in FIG. 8B. The MRA has a shallow resonance just above 153 MHz and is the same with the solenoid present, as indicated by trace 881; and, trace 881 is indistinguishable from trace 882 indicating the response for the MRA with solenoid and water. In contrast, there is a deeper resonance at 153 MHz for the solenoid alone as indicated by trace 871. The peak is diminished and moved by the presence of the MRA as indicated by traces 872, 873, 874 and 875 (very close to trace 873). These results indicate that the MRA resonance frequencies are unaffected by the nearby solenoid or water loading media; while the solenoid frequencies are shifted and strongly couple to the MRA and water.

An embodiment is described to exploit particular NQR bands for explosive detection and discrimination. Long acquisition times have been a continuing issue in field implementation of NQR. If a potential LED's explosive is unknown, this can cause extremely long acquisition times. Currently, if one were to check for all known common explosives, multiple pulse sequences at specific NQR frequencies would have to be run sequentially for each potential explosive. This leads to long acquisition times that are not practical in an operational scenario. In contrast, the demonstrated MRA embodiments enable the achievement of short acquisition times—not just for one compound, but for multiple explosive compounds simultaneously. An example embodiment includes an MRA array composed with eight antenna elements resonant at 1.84 MHz, 3.41 MHz and 5.05 MHz, 1,563 MHz, 3.787 MHz and 5.199 MHz, 3.6 MHz and 4.64 MHz, separated by a small spacing. Such resonant frequency metamaterial antennae can distinguish several different explosives, as demonstrated in FIG. 9; each antenna element exploits its unique designed frequency to identify one or more of the eight spectral frequencies, FIG. 9 is a set of aligned graphs 910, 920, 930 that illustrates example resonances of $^{14}$N in various target materials and corresponding metamaterial antennae resonances for identification, according to various embodiments. The target materials include three explosives, RDX, HMX and Sodium Nitrate, in graphs 910, 920 and 930, respectively. RDX is an acronym for Research Department Explosive, and is an explosive nitroamine widely used in military and industrial applications. HMX, also called octogen, is a powerful and relatively insensitive nitroamine high explosive, chemically related to RDX. HMX has been considered an acronym variously listed as High Melting eXplosive, Her Majesty's eXplosive, High-velocity Military eXplosive, or High-Molecular-weight rdX. Each graph has a horizontal axis 902 that indicates frequency in MHz and a vertical axis 904 that indicates relative amplitude of a NQR response in arbitrary units. The NQR peaks for $^{14}$N in Sodium Nitrate occur at frequency 931 and 932 in graph 930, and both are included among the eight proposed resonances of one or more metamaterial antennae, such as one or more MRA. At least frequency 932 is unique and easily distinguished from other explosives. The NQR peaks for $^{14}$N in HMX occur at frequencies 921, 922, 923, 92.4 and 926 in graph 920. Of these 921 and 923 are included among the eight proposed resonances of one or more metamaterial antennae, such as one or more MRA. Both are unique and easily distinguished from locations of NQR peaks for other explosives. The NQR peaks for $^{14}$N in RDX occur at frequencies 911, 912, 913, 914, 915, 916 and 917 in graph 910. Of these 912, 913, 915 and 916 are included among the eight proposed resonances of one or more metamaterial antennae, such as one or more MRA. Both are unique and easily distinguished from locations of NQR peaks other explosives.

The non-loading behavior is an advantage that allows one to design and engineer multiple MRA frequencies to target specific NQR frequencies, as shown in FIG. 9. This figure shows that for 3 different explosive compounds the MRA resonances are engineered to align with specific NQR frequencies that do not overlap with each other. Multiple MRA resonances (solid "V" lines) are engineered to match specific NQR frequencies (vertical dashed lines). In addition, the non-loading behavior of these MRAs allows the MRAs to stack into a single architecture without affecting the ability to identify multiple materials. The ability to design MRAs with appropriate spectral line widths gives the flexibility to choose which NQR resonances are to be interrogated for positive identification. It is advantageous to choose NQR frequencies that do not overlap in the different materials. In addition, the MRA spectral line widths are engineered to encompass shifts caused by temperature variations to enhance proper identification and reduce false identification. In addition, new RF switching technologies are anticipated, which could be used to tune the resonance of the MRAs (and also any meta-lenses) to accommodate shifts associated with the NQR frequencies due to temperature changes and other environmental factors.

Performance of the GPR system (for detection) and the NQR system (for subsequent identification) is maintained regardless of normal operating temperatures, nearby devices, other broadcasting antennas, and typical antenna loading media and environments.

4. Digital Hardware Overview

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitute computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals, that carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC 1020.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

Some embodiments are related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1.008. Execution of the sequences of instructions contained in memory 1004 causes processor 1002 to perform the method steps described herein. In alternative embodiments, hardware, such as application specific integrated circuit 1020, may be used in place of or in combination with software to implement an embodiment. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

FIG. 11 illustrates a chip set 1100 upon which an embodiment of the invention may be implemented. Chip set 1100 is programmed to perform one or more steps of a method described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of a method described herein.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1105 also stores the data associated with or generated by the execution of one or more steps of the methods described herein.

5. Extensions, Modifications and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A system comprising a plurality of metamaterial antennae to both transmit and receive a corresponding plurality of magnetic fields focused at a corresponding plurality of near-field distances separated from the plurality of antennae, at a corresponding plurality of different antenna frequencies corresponding to a plurality of nuclear quadrupole resonance frequencies of an atom in a target material, wherein at least one metamaterial antenna of the plurality of metamaterial antennae comprises a substrate with a singular first ring element connected to a first side of the substrate and a second ring element each respectively connected to an opposing second side of the substrate.

2. The system as recited in claim 1, wherein the plurality of metamaterial antennae simultaneously transmit signals at the different antenna frequencies and subsequently receive return signals at the different antenna frequencies to detect a nuclear quadrupole spectrum of frequencies associated with the target material at the near-field distance.

3. The system as recited in claim 1, wherein the plurality of metamaterial antennae substantively eliminate de-tuning from loading effects from a nearby broadcasting antenna or water in a medium within the near-field distance, of the plurality of metamaterial antennae.

4. The system as recited in claim 1, further comprising at least one metamaterial lens disposed between the plurality of metamaterial antennae and a subject that includes the target material, wherein the at least one metamaterial lens at least one of amplifies focused near-field energy of an individual antenna frequency corresponding to a weak nuclear quadrupole resonance frequency and increases a corresponding antenna near-field distance.

5. The system as recited in claim 1, further comprising a processor to identify the target material present in a vicinity of the near-field distance based at least in part on the received magnetic field at the plurality of metamaterial antennae focused at the near-field distance and a nuclear quadrupole resonance spectrum for the target material.

6. The system as recited in claim 1, wherein the atom is Nitrogen 14 ($^{14}$N).

7. The system as recited in claim 1, wherein the target material is a narcotic.

8. The system as recited in claim 1, wherein the target material is an explosive.

9. The system as recited in claim 1, wherein the plurality of metamaterial antennae comprise an impedance that matches an impedance of a feeder line to the plurality of metamaterial antennae.

10. The system as recited in claim 9, wherein at least one of the metamaterial antennae and the feeder line have an impedance of 50 ohms.

11. The system as recited in claim 1, further comprising a ground penetrating radar (GPR) metamaterial antenna to both transmit and receive an electromagnetic field at a GPR frequency to interrogate a region of interest for broad area assessment for a suspect target material.

12. The system as recited in claim 1, wherein the plurality of metamaterial antennae are stacked closely together so that the corresponding magnetic fields substantively overlap in space.

13. A method comprising:

interrogating a region of interest (ROI) with a ground penetrating radar (GPR) antenna to detect a suspect target material in a vicinity of the GPR antenna;

transmitting a plurality of nuclear quadrupole resonance (NQR) frequencies from a plurality of stacked metamaterial antennae focused at the suspect target material, at least one metamaterial antenna of the plurality of metamaterial antennae comprises a substrate with a singular first ring element connected to a first side of the substrate and a second ring element each respectively connected to an opposing second side of the substrate;

receiving, by the plurality of stacked metamaterial antennas, magnetic fields of NQR frequency signals from the suspect target material to capture a NQR frequency spectrum; and identifying, by a processor, the suspect target material based on the captured NQR frequency spectrum.

14. The method as recited in claim 13, wherein identifying the suspect target material includes identifying a chemical compound in the suspect target material.

15. The method as recited in claim 13, wherein transmitting the plurality of nuclear quadrupole resonance (NQR) frequencies from the plurality of stacked metamaterial antennas include transmitting, simultaneously, the plurality of NQR frequencies.

16. The method as recited in claim 13, wherein the GPR antenna is a metamaterial antenna stacked with the plurality of stacked metamaterial antennae.

\* \* \* \* \*

UNITED STATES PATENT AND TRADEMARK OFFICE
CERTIFICATE OF CORRECTION

PATENT NO. : 9,945,917 B2
APPLICATION NO. : 14/150704
DATED : April 17, 2018
INVENTOR(S) : Christina Hartsell Drake, Clara Rivero Baleine and Nelson Ch Poon Page 1 of 1

It is certified that error appears in the above-identified patent and that said Letters Patent is hereby corrected as shown below:

In the Claims

Column 24, Claim 3, Line 34, delete "," after "distance."

Signed and Sealed this
Nineteenth Day of March, 2019

Andrei Iancu
*Director of the United States Patent and Trademark Office*